(12) United States Patent
Suzuki et al.

(10) Patent No.: US 7,301,018 B2
(45) Date of Patent: Nov. 27, 2007

(54) PROBE FOR MASS SPECTROMETRY OF LIQUID SAMPLE

(75) Inventors: Koji Suzuki, Kawasaki (JP); Yoshio Suzuki, Yokohama (JP)

(73) Assignees: Japan Science and Technology Corporation, Kawaguchi-Shi (JP); The Kanagwa Academy of Science and Technology Foundation, Kawasaki-shi (JP)

( * ) Notice: Subject to any disclaimer, the term of this patent is extended or adjusted under 35 U.S.C. 154(b) by 493 days.

(21) Appl. No.: 10/332,622

(22) PCT Filed: Jul. 10, 2001

(86) PCT No.: PCT/JP01/05961

§ 371 (c)(1),
(2), (4) Date: Sep. 5, 2003

(87) PCT Pub. No.: WO02/04936

PCT Pub. Date: Jan. 17, 2002

(65) Prior Publication Data

US 2004/0142378 A1    Jul. 22, 2004

(30) Foreign Application Priority Data

Jul. 11, 2000 (JP) .............................. 2000-210592

(51) Int. Cl.
  G01N 27/62 (2006.01)
  G01N 30/72 (2006.01)
  H01J 49/00 (2006.01)

(52) U.S. Cl. .......................... 536/124; 536/123.1; 564/1
(58) Field of Classification Search ..................... None
See application file for complete search history.

(56) References Cited

FOREIGN PATENT DOCUMENTS

| JP | 5-87794 A | | 4/1993 |
| JP | 6-102251 A | | 4/1994 |
| JP | 8-145948 A | | 6/1996 |
| JP | 08-145948 A | * | 6/1996 |
| JP | 8-145949 A | | 6/1996 |
| WO | WO99/32501 | * | 7/1999 |

* cited by examiner

Primary Examiner—Richter Johann
Assistant Examiner—Yevgeny Valenrod
(74) Attorney, Agent, or Firm—Birch, Stewart, Kolasch & Birch, LLP

(57) ABSTRACT

Disclosed is a probe for mass spectrometry of liquid samples, which may effectively ionize the sample without adding a protic solvent to the mobile phase in the ionization method in mass spectrometry of liquid samples. The probe according to the present invention has a structure represented by the Formula [I]:

$$R^2\text{-}A\text{-}R^1 \quad [I]$$

(wherein $R^1$ represents an ionic functional group which becomes an ion in a solvent, $R^2$ represents a structure which can bind to other substance, and A represents an arbitrary spacer moiety).

27 Claims, 3 Drawing Sheets

PROBE FOR MASS SPECTROMETRY OF LIQUID SAMPLE

This application is the national phase under 35 U.S.C. § 371 of PCT International Application No. PCT/JP01/05961 which has an International filing date of Jul. 10, 2001, which designated the United States of America.

TECHNICAL FIELD

The present invention relates to a probe for mass spectrometry of liquid samples.

BACKGROUND ART

At present, one of the methods by which a sample in a specimen may be quantified with the highest sensitivity and accuracy is mass spectrometry. What is important for the measurement of a liquid sample by mass spectrometry is to select an ionization method suited for the characteristics of the compound. For example, when classified based on the factors by which the compound is made unstable, the ionization methods are largely classified into hard ionization and soft ionization. The former includes electron ionization method, chemical ionization method and atmospheric pressure ionization method, and the latter includes electrospray ionization method, matrix-assisted laser desorption ionization method and fast atom bombardment ionization.

On the other hand, a method (LC/MS) in which the sample separated by high performance liquid chromatography is subjected to mass spectrometry on the same the ionization method suited for the liquid chromatography is a method for directly ionizing the sample solution flowing out from the tip of a capillary, the ionization method is classified into the latter method in the methods described above. In particular, the apparatus in which an electrospray ionization mass spectrometer and an apparatus for high performance liquid chromatography are connected on line is most widely used, and well exhibits its power in identification of substances indispensable to the body, such as proteins and saccharides, as well as of environmental hormones. In the electrospray ionization, the possibility that the molecular ion peak of the sample is detected is extremely low, and the sample is detected as a pseudo-molecular ion peak in which sodium is usually attached.

Alternatively, in LC/MS, ionization of the sample is aided by admixing a protic solvent such as ammonium acetate, formic acid or acetic acid to the mobile phase.

As a method for aiding ionization in the mass spectrometry of a liquid sample, it is now common to add a protic solvent to the mobile phase of liquid chromatography in LC/MS. However, the following drawbacks have been pointed out: i) when using ammonium acetate in anion mode, the ion of the sample and the ammonium ion are paired, so that the sensitivity is decreased; ii) when using trifluoroacetic acid in cation mode, the sample ion and the trifluoroacetic acid ion are paired, so that the sensitivity is decreased, and in anion mode, ionization is prevented except for some cases; and iii) in case of using acetonitrile, an acid must be added, and in this case, ammonium acetate cannot be used because it is not dissolved therein.

DISCLOSURE OF THE INVENTION

Accordingly, an object of the present invention is to provide means for effectively ionizing a sample without adding a protic solvent to the mobilize phase in an ionization method in mass spectrometry of a liquid sample.

The present inventors intensively studied to reach the idea that the sample compound may be effectively ionized by using as a probe a compound having, in one molecule, a group which is ionized in a solvent, and a functional group which reacts with a functional group in the sample compound to covalently bind thereto, and by making the probe covalently bind to the sample compound, and experimentally confirmed that the sample compound ionized by such a probe can be quantified by electrospray mass spectrometry with high sensitivity, thereby completing the present invention.

That is, the present invention provides a probe for mass spectrometry of liquid samples, which is represented by the Formula [I]:

$$R^2\text{-A-}R^1 \quad\quad [I]$$

(wherein $R^1$ represents an ionic functional group which becomes an ion in a solvent, $R^2$ represents a structure which can bind to other substance, and A represents an arbitrary spacer moiety). The present invention also provides a method for mass spectrometry, comprising binding the probe according to the present invention to a sample compound in a sample liquid; and subjecting the obtained bound product to mass spectrometry. The present invention further provides a use of the compound represented by the Formula [I] for the production of a probe for mass spectrometry of liquid samples.

By using the probe according to the present invention, the sample can be effectively ionized without adding a protic solvent in the mobile phase in the electrospray ionization method, so that electrospray ionization mass spectrometry can be carried out for various samples with high sensitivity and high accuracy.

BEST MODE FOR CARRYING OUT THE INVENTION

Figure 1:
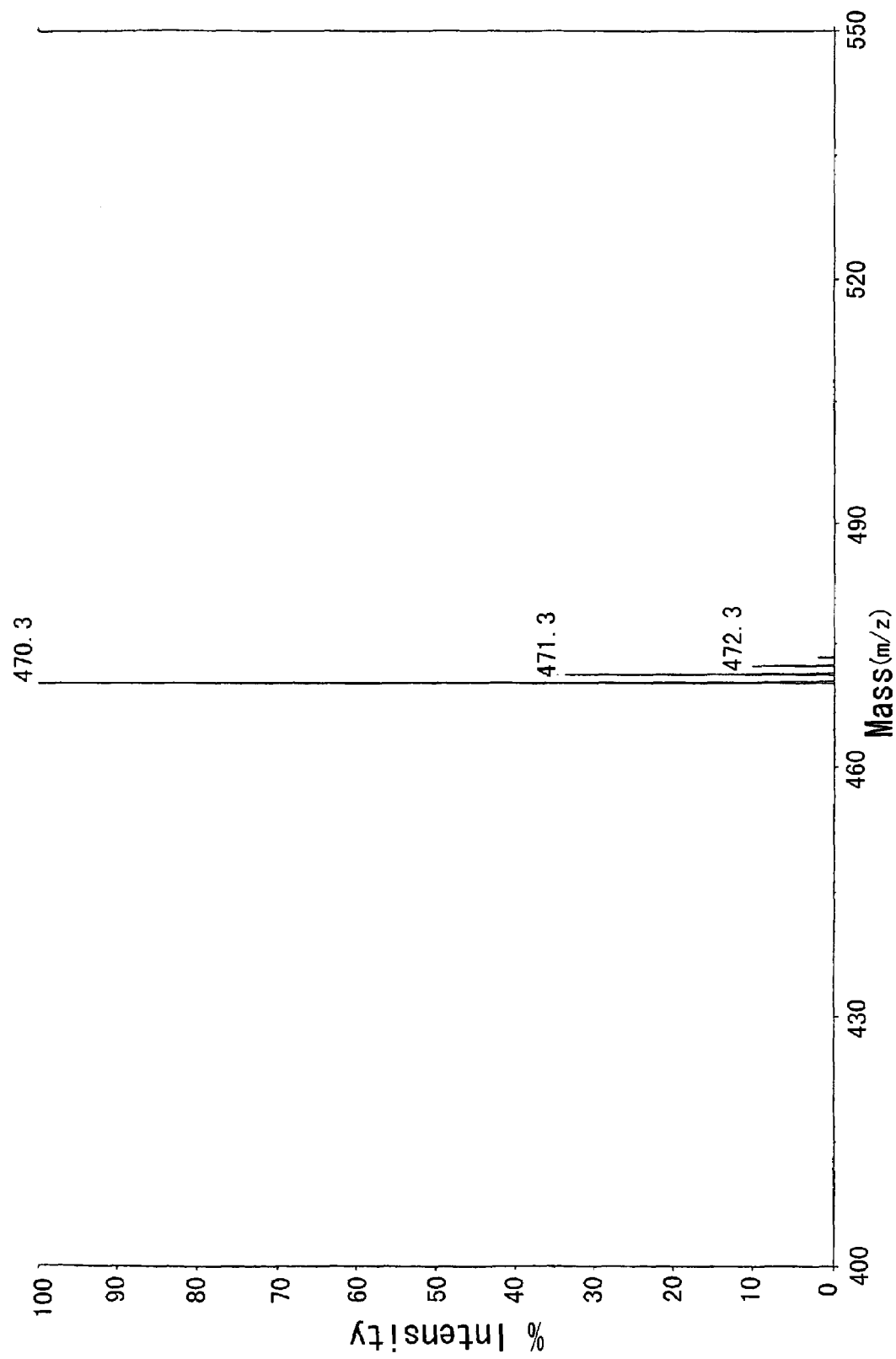
FIG. 1 shows the mass spectrum obtained in the electrospray ionization mass spectrometry carried out in Example 11 according to the present invention.

The probe for ionization mass spectrometry of liquid samples according to the present invention is represented by the above-described Formula [I]. In Formula [I], $R^1$ represents an ionic functional group which becomes an ion in a solvent. $R^1$ is a group to be ionized in the solvent. $R^1$ may be any group as long as it is ionized in the solvent used, and may be either a group to be positively charged or a group to be negatively charged. Examples of $R^1$ include amines, carboxylic acid and salts thereof, sulfonic acid and salts thereof, and

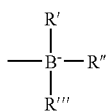

(wherein R', R" and R'" represent arbitrary groups which do not adversely affect the present invention, which may be the same or different, preferably hydrogen, halogen, or $C_1$-$C_{20}$ linear or branched alkyl), but $R^1$ is not restricted to thereto (It should be noted that "halogen" may be any of fluorine, chlorine, bromine and iodine, unless otherwise specified). Among these, amines are preferred, and especially, the amines represented by the following Formula [II] are preferred

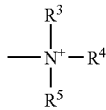

[II]

(wherein $R^3$, $R^4$ and $R^5$ independently represent arbitrary groups which do not adversely affect the present invention, and preferably hydrogen, halogen, or $C_1$-$C_{20}$ linear or branched alkyl), In the above-described Formula [I], $R^2$ represents a structure which can bind to other substance. A preferred family of the examples of $R^2$ are the functional groups which can react with the substance so as to covalently bind to the substance.

In this case, any functional group may be employed as $R^2$ as long as it can react with the substance so as to covalently bind to the substance. Since the liquid samples to be analyzed by mass spectrometry are biological substances such as proteins and saccharides in most cases, $R^2$ is preferably a functional group which reacts with and covalently bind to a functional group that is often included in these substances, that is, —$NH_2$, —SH, —COOH, —OH, —CHO and the like. Examples of such a functional group include SCN—, $ClO_2S$—,

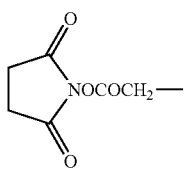 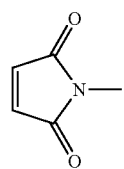

$BrH_2C$—, ClOC—, —$NH_2$, —$NHNH_2$, —$CH_2I$, —$CH_2ONH_2$(—HCl)(which may or may not be hydrochloric acid salt),

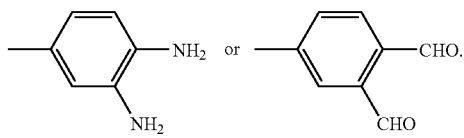

The functional groups (R') in sample compounds, which react with these functional groups as well as the resulting bonds formed by the reactions are shown in Table 1 below (In cases where $R^2$ is —$NH_2$, it can bind to the $R^2$ listed in Table 1 as the functional group which may be employed when the functional group (R') in the sample compound is —$NH_2$).

TABLE 1

| Functional Group (R2) | Functional Group (R') | Formed Bond |
|---|---|---|
| SCN— | —NH₂ | —N—O—N—<br>\|  \|\|  \|<br>H   S   H |
| ClO₂S— | —NH₂ | O<br>\|\|<br>—S—N—<br>\|\|  \|<br>O   H |
| (succinimidyl-NOCOCH₂—) | —NH₂ | —C—C—N—<br>H₂ \|\|  \|<br>    O   H |
| (maleimide) | —SH | (succinimide with S—) |
| BrH₂C— | —COOH | —C—O—C—<br>H₂      \|\|<br>         O |
| IH₂C— | —COOH | —C—O—C—<br>H₂      \|\|<br>         O |
| ClOC— | —OH | —C—O—<br>\|\|<br>O |
| (o-diaminobenzene) | —CHO | (benzimidazole) |
| (o-dialdehyde benzene) | —NH₂ | (benzotriazole-like) |

TABLE 1-continued

| Functional Group (R2) | Functional Group (R') | Formed Bond |
|---|---|---|
| —CH$_2$ONH$_2$(—HCl) | 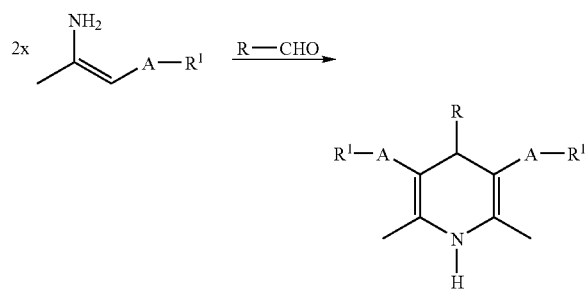 | |
| —NHNH$_2$ | —CHO | |

As the $R^2$, CH$_3$CH(NH$_2$)=CH— may also preferably be employed. In this case, 2 molecules of the probe react with the sample compound represented by R—CHO as follows:

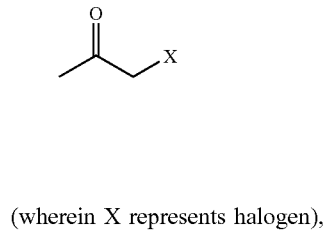

Additional preferred examples of $R^2$ include the groups represented by Formula [VI]:

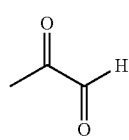

[VI]

(wherein X represents halogen),

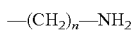

and represented by Formula [VII]:

—(CH$_2$)$_n$—NH$_2$  [VII]

(wherein n represents an integer of 1 to 5).

In Formula [VI], the halogen is preferably bromine.

The $R^2$ represented by the above-described Formula [VI] reacts with cytosine in a sample compound as follows:

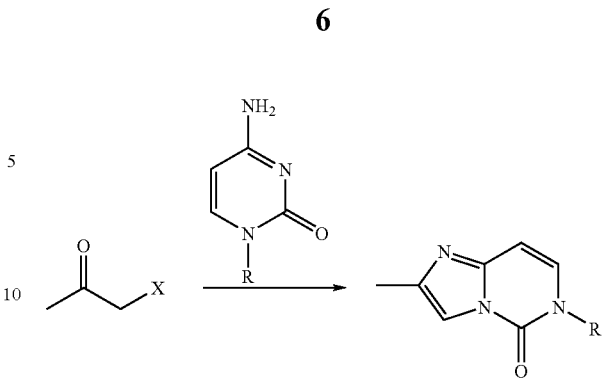

(wherein R represents an arbitrary group such as the sugar moiety of a nucleotide or nucleic acid).

Since this $R^2$ can bind to cytosine moiety of a sample compound, it can bind to cytidine monophosphate, cytidine diphosphate, cytidine triphosphate, deoxycytidine monophosphate, deoxycytidine diphosphate and deoxycytidine triphosphate, as, well as to nucleic acid such as DNA and RNA containing cytosine.

In cases where $R^2$ is the above-described

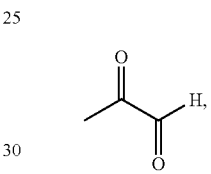

it reacts with guanine in a sample compound and binds thereto as follows:

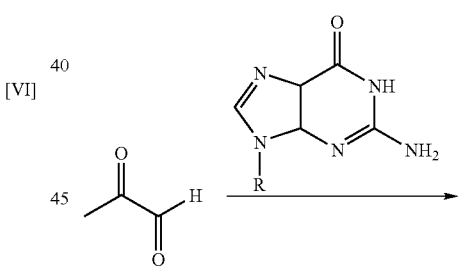

(wherein R represents an arbitrary group such as the sugar moiety of a nucleotide or nucleic acid).

Since this $R^2$ can bind to guanosine monophosphate, guanosine diphosphate, guanosine triphosphate, deoxyguanosine monophosphate, deoxyguanosine diphosphate and deoxyguanosine triphosphate, as well as to nucleic acid such as DNA and RNA containing guanine.

In cases where $R^2$ is the group represented by the above-described Formula [VII], it reacts with phosphate moiety of a sample compound and bind thereto as follows: (In the example below, the case wherein n is 2 is shown.)

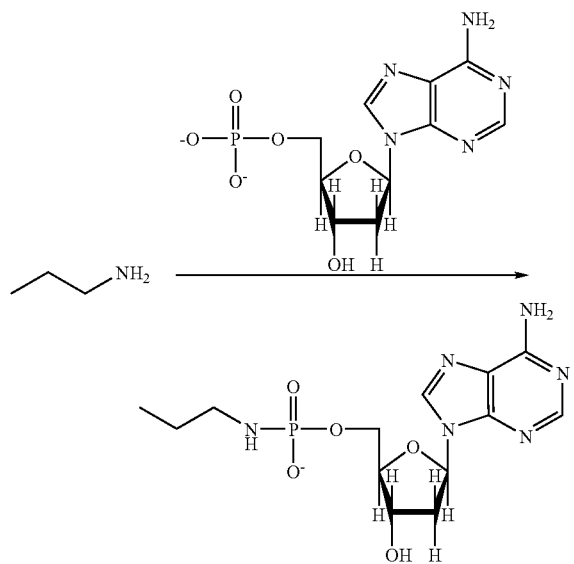

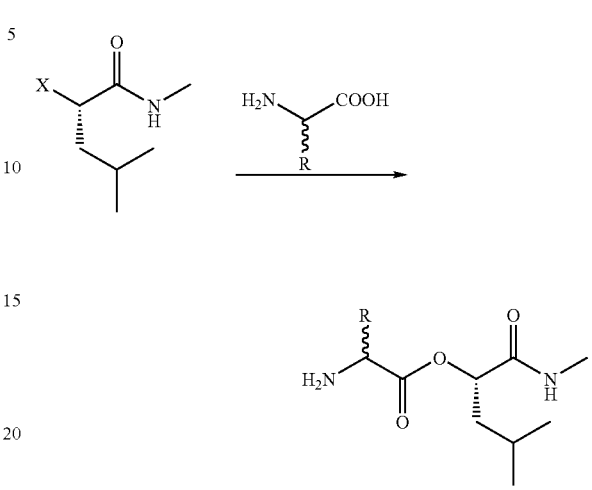

Although this reaction equation shows the case wherein the sample compound is deoxyadenosine monophosphate (that is, the base in the nucleotide is adenine and the sugar is deoxyribose), the base may be any base other than adenine, such as cytosine, guanine, thymine or uracil, and the sugar may be deoxyribose or ribose, because the $R^2$ binds to phosphate moiety. Similarly, although the number of phosphate in the above-described reaction equation is 1, the number of condensed phosphate may be any of 1 to 3 because the $R^2$ binds to terminal phosphate. Thus, the $R^2$ represented by Formula [VII] can bind to any types of nucleoside monophosphate, nucleoside diphosphate and nucleoside triphosphate. Further, since there exists a free phosphate in nucleic acids, the $R^2$ represented by Formula [VII] can bind to nucleic acids such as DNA and RNA.

In cases where $R^2$ is a group having optical activity, a sample compound having a specific optical activity can be measured by binding the $R^2$ to the sample compound having optical activity. Moreover, the absolute configuration of the optical center in the sample compound can be determined.

Preferred examples of $R^2$ having optical activity include the groups represented by Formula [VIII]:

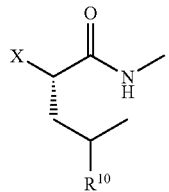

[VIII]

(wherein X represents halogen, and $R^{10}$ represents $C_1$-$C_5$ alkyl).

As the halogen, bromine is especially preferred.

The $R^2$ represented by Formula [VIII] reacts with an amino acid and bind thereto as follows:

(wherein R represents an arbitrary side chain of the amino acid).

In this case, if the amino acid is a mixture (racemate) of D-isomer and L-isomer, the formed binding products are diastereomers each other. By carrying out LC/MS in this state, not only the product can be detected with a high sensitivity by a mass spectrometry such as ESI, but also the absolute configuration of the amino acid can be determined.

The $R^2$ is not restricted to the functional groups which can react with a functional group in the sample compound and covalently bind thereto, but the groups which bind to the sample compound by intercalation or by coordinate bond, as well as the groups having cyclic structures that clathrate the sample compound may also preferably be employed as $R^2$.

That is, preferred examples of $R^2$ include those having structures which intercalate into double-stranded nucleic acids. Concrete examples of such $R^2$ include the groups represented by Formula [IX] below:

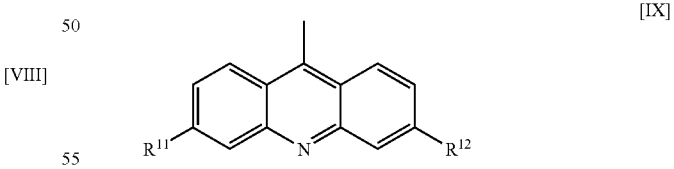

[IX]

(wherein $R^{11}$ and $R^{12}$ independently represent hydrogen, halogen, $C_1$-$C_5$ alkyl or $C_1$-$C_5$ N,N-dialkylamino).

Since such $R^2$ binds to double-stranded nucleic acids by intercalation, a probe having such $R^2$ may preferably be employed for the measurements of double-stranded nucleic acids.

Examples of the groups having cyclic structures that clathrate the sample compound include the groups represented by Formula [X] below:

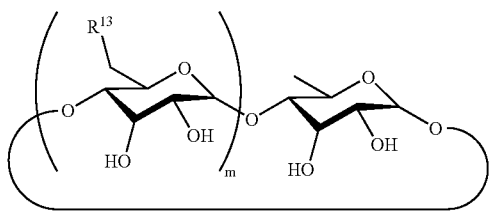

[X]

(wherein $R^{13}$ represents hydroxyl, carboxyl or $C_1$-$C_5$ alkyl; and m represents an integer of 5 to 9).

The cyclodextrin structure shown by Formula [X] is a cyclic oligosaccharide having a truncated cone structure in which hydroxyl groups face outward and carbon chains face inward. Since the hole in the cyclodextrin is a hydrophobic field, it can clathrate an organic molecule in the hole utilizing hydrophobic interaction. Utilizing this phenomenon, a probe having the above-described $R^2$ may be used for purifying water containing various small amounts of organic molecules, and for identifying the substances contained therein. By adding the probe in an aqueous sample and stirring the mixture, the organic molecules in the aqueous sample are clathrated in the holes of the cyclodextrin molecules.

Further examples of the groups having cyclic structures which clathrate sample compounds include the groups represented by Formula [XI] below.

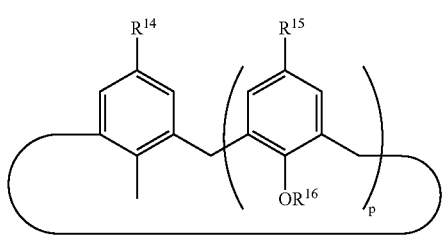

[XI]

(wherein $R^{14}$ and $R^{15}$ independently represent hydrogen, halogen or $C_1$-$C_5$ alkyl; $R^{16}$ represents $C_1$-$C_5$ alkyl or $C_1$-$C_5$ alkyl which has a carboxyl group, ester group or an amide group at its terminal; and p represents an integer of 3 to 7).

The calixarene represented by Formula [XI] is a cyclic oligomer comprising benzene rings. The hole encircled by the benzene rings of the calixarene is a hydrophobic field, it can clathrate an organic molecule in the hole utilizing hydrophobic interaction. Utilizing this phenomenon, a probe having the above-described $R^2$ may be used for purifying water containing various small amounts of organic molecules, and for identifying the substances contained therein. By adding the probe in an aqueous sample and stirring the mixture, the organic molecules in the aqueous sample are clathrated in the holes of the calixarene.

The group having a cyclic structure which clathrate a sample compound is not restricted to those described above. For example, a group formed by eliminating one hydrogen atom from crown ether or the like may also be employed.

Further, as $R^2$, the groups obtained by eliminating one hydrogen atom from a complex-forming compound such as EDTA, which forms a coordinate bond with the sample compound may also be employed.

In Formula [I], A represents an arbitrary spacer moiety. Since the probe according to the present invention binds to the sample compound by $R^2$ and ionizes the compound after binding to the sample compound by $R^1$, the A located between $R^1$ and $R^2$ may have an arbitrary structure. It is preferred, however, that A comprise a hydrophobic moiety and hydrophilic moiety because the probe may be used for both hydrophobic solvent and hydrophilic solvent, so that the universality of the probe is increased. Examples of the hydrophobic moiety include aromatic rings such as benzene ring. Examples of the hydrophilic moiety include structures containing ether, amine or ketone. Preferred examples of such A include those represented by Formula [III] below:

[III]

(wherein $R^6$ represents $C_1$-$C_{20}$ alkylene with the proviso that not less than one and not more than half of the —$CH_2$— units therein may be-substituted by one or more groups selected from the group consisting of —O—, —CO— and —NH—, and that the alkylene may be substituted by one or more $C_1$-$C_{20}$ alkyl; and Ar represents an aromatic ring which may be substituted by 1 to 5 $C_1$-$C_6$ alkyl).

Preferred examples of the A represented by Formula [III] include those represented by the following Formula [IV]:

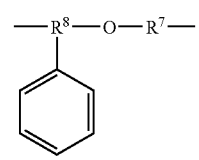

[IV]

(wherein $R^7$ may or may not exist, and when it exists, it represents $C_1$-$C_6$ alkylene; and $R^8$ represents $C_1$-$C_6$ alkylene in which an arbitrary hydrogen is substituted by the benzene ring shown in Formula [IV]), or represented by the following Formula [V]:

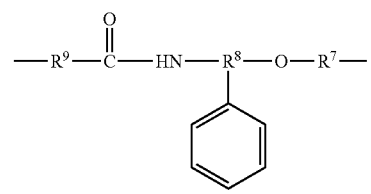

[V]

(wherein $R^7$ and $R^8$ represent the same meanings as in Formula [IV]; $R^9$ may or may not exist, and when it exists, it represents $C_1$-$C_6$ alkylene).

As the A, those wherein $R^9$ is phenylene group in the above-described Formula [V] may also preferably be employed. This A may especially preferably be employed when $R^2$ has the structure represented by the above-described Formula [VI] and $R^2$ is

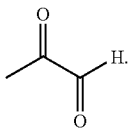

As the A, those represented by —R— may also preferably be employed (wherein $R^6$ represents the same meanings as $R^3$ in Formula [III]). This A may especially preferably be employed when $R^2$ is a group having the structure which intercalates into double-stranded nucleic acids (e.g., the group represented by the above-described Formula [IX]) and the sample compound is a double-stranded nucleic acid, and when $R^2$ is a group having a cyclic structure which clathrate other substance (e.g., the group represented by the above-described Formula [X]or [XI]).

As the A, those represented by —$R^6$—Ar—$R^{6'}$— (wherein $R^6$ and Ar represent the, same meanings as in Formula [III]; $R^{6'}$ may or may not exist, and when it exists, it represents the same meanings as the $R^6$ in Formula [III] (with the proviso that $R^6$ and $R^{6'}$ in the formula may be the same or different) may also be preferably employed. Preferred examples of such A include those represented by Formula [XII] below:

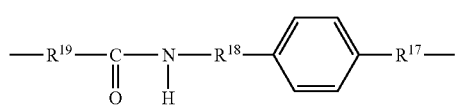
[XII]

(wherein $R^{17}$ and $R^{18}$ independently represent $C_1$-$C_6$ alkylene; and $R^{19}$ may or may not exist, and when it exists, it represents $C_1$-$C_6$ alkylene);

or represented by the following Formula [XIII]:

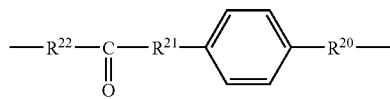
[XIII]

(wherein $R^{20}$ and $R^{21}$ independently represent $C_1$-$C_6$ alkylene; and $R^{22}$ may or may not exist, and when it exists, it represents $C_1$-$C_6$ alkylene).

Although the A may have an arbitrary structure, if the molecular weight of the overall probe is too large, the percentage of the weight of the probe in the sample compound-probe binding product is large so that the sensitivity of the analysis is decreased. Therefore, the molecular weight of the probe is preferably not more than 1000.

The probe according to the present invention may easily be produced by those skilled in the art based on known methods. In the Examples below, production processes for producing a plurality of preferred probes are concretely described.

The reaction between the sample compound and the probe may be carried out under appropriate conditions based on known technologies depending on the $R^2$ of the probe and the type of the functional group to be bound to $R^2$. In the Examples below, conditions for the binding reactions between preferred probes and sample compounds are concretely described.

Examples of the conditions for the respective binding reactions for the above-described concrete combinations of $R^2$ and the functional group (R') in the sample compound binding to the $R^2$ will now be described. However, since these conditions are merely examples and since the functional groups can be bound under other conditions, it is apparent for those skilled in the art that the conditions for the binding reactions are not restricted to those described below. Further, as for the $R^2$ s not described here, those skilled in the art may easily carry out the binding reactions according to common chemical knowledge.

(1) In cases where $R^2$ is SCN— and R' is —$NH_2$

To 2 to 3 mg of a sample, 0.2 ml of (ethanol:water: triethylamine 2:2:1 v/v) is added and the resulting mixture is evaporated to dryness under reduced pressure. Thereafter, 0.5 ml of (ethanol:water:triethylamine:probe=7:7:1:1 v/v) is added, and the mixture is allowed to react at room temperature for 20 minutes. The solvent is then evaporated under reduced pressure and the residue is dissolved in an eluent to obtain a sample solution (see B. A. Bidlingmeyer, et al, J. Chromatogr., 336, 93 (1984)).

(2) In cases where $R^2$ is $ClO_2S$— and R' is —$NH_2$

To 2 to 3 mg of a sample, 500 μL of 1M aqueous $NaHCO_3$ solution and 200 μL of 1 mg/mL probe solution in acetone are added, and the resulting mixture is heated at 60° C. for 30 minutes. After evaporating the acetone, the residue is dissolved in an eluent to obtain a sample solution (see Meffin, P. J., et al, J. Pharm. Sci., 66, 583 (1977).

(3) In cases where $R^2$ is

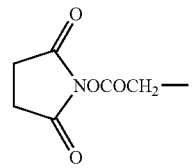

and R' is —$NH_2$

In 5.0 mL of THF, 1.5 mg of a sample is dissolved and 50 mg of probe is added, followed by heating the mixture at 60° C. for 30 minutes. After evaporating THF, the residue is dissolved in an eluent to obtain a sample solution (see Jupill, T. H., Am. Lab., 8 (5), 85-92 (1976)).

(4) In cases where $R^2$ is

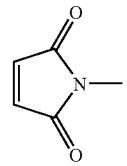

and R' is —SH

In 500 μL of water, 2 to 3 mg of a sample is dissolved, and 200 μL of 1 mg/mL probe solution in acetonitrile is added, followed by heating the resulting mixture at 60° C. for 30 minutes. The solvent is evaporated and the residue is dissolved in an eluent to obtain a sample solution (see Nakashima K., et al, Talanta., 32, 167 (1985)).

(5) In cases where $R^2$ is $BrH_2C$— or $IH_2C$— and R' is —COOH

In 500 μL of acetone, 2 to 3 mg of a sample is dissolved, and 200 μL of 1 mg/mL probe solution in acetone and 1 mg of $K_2CO_3$ are added, followed by heating the resulting mixture at 60° C. for 30 minutes. The solvent is evaporated and the residue is dissolved in an eluent to obtain a sample solution (see Dunges, W., Anal. Chem., 49, 442 (1977)).

(6) In cases where $R^2$ is ClOC— and R' is —OH

In 0.5 ml of pyridine, 2 to 3 mg of a sample is dissolved and 0.2 mL of 1 mg/mL probe solution in pyridine is added, followed by heating the resulting mixture at 40° C. for 1 hour. The solvent is evaporated and the residue is dissolved in an eluent to obtain a sample solution (see Suzuki, A., et al., J. Biochem., 82, 1185 (19773).

(7) In cases where $R^2$ is

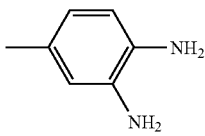

and R' is —CHO

To 1.0 ml of methanol, 0.1 ml of acetic acid and 0.2 mL of 1 mg/mL probe solution in methanol, 2 to 3 mg of a sample is added, and the resulting mixture is heated at 40° C. for 30 minutes. The solvent is evaporated and the obtained residue is dissolved in an eluent to obtain a sample solution.

(8) In cases where $R^2$ is

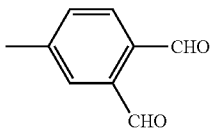

and R' is —$NH_2$

To 0.1 ml of a sample solution in ethanol ($10^{-4}$ to $10^{-3}$M), 1.5 mL of 10 mg/mL probe solution in ethanol is added, and the resulting mixture is stirred at room temperature for 5 to 10 minutes. The solvent is evaporated under reduced pressure and the residue is dissolved in an eluent to obtain a sample solution (see Roth, M., Anal. Chem., 43, 880 (1971)).

(9) In cases where $R^2$ is —$CH_2ONH_2$. HCl and R' is

A mixture of 1 to 5 mg of a sample, two drops of triethylamine and 50 mg of a probe is heated at 50° C. for 30 minutes. The solvent is evaporated under reduced pressure and the residue is dissolved in an eluent to obtain a sample solution (see Jupille, T. H., Am. Lab., 8 (5), 85-92 (1976)).

(10) In cases where $R^2$ is —$NINH_2$ and R' is —CHO

In 0.5 ml of water, 1 to 5 mg of a sample was dissolved, and 30% aqueous $HClO_4$ solution in which a probe is dissolved at a concentration of 20 mg/mL was added thereto, followed by stirring the resulting mixture at room temperature for 10 minutes. The solvent is evaporated under reduced pressure and the residue is dissolved in an eluent to obtain a sample solution (see Newberg, C., et al., Anal. Chim. Acta, 7, 238 (1952)).

(11) In cases where $R^2$ is

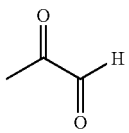

and R' is

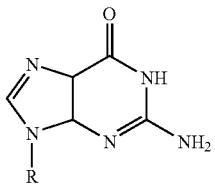

In 50 μL of phosphate buffer (pH7.0), 0.1 to 5.0 μg of a sample is dissolved, and 200 μL of 1 mg/mL probe solution in phosphate buffer (pH7.0) is added thereto, followed by stirring the resulting mixture at room temperature for 5 minutes. The solvent is evaporated under reduced pressure and the residue is dissolved in an eluent to obtain a sample solution.

(12) In cases where $R^2$ is

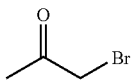

and R' is

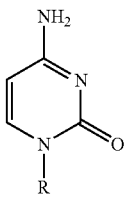

In 50 mL of phosphate buffer (pH 7.0), 0.1 to 5.0 μg of a sample is dissolved, and 200 μL of 1 mg/mL probe solution in phosphate buffer (pH 7.0) is added thereto, followed by stirring the resulting mixture at room temperature for 5 minutes. The solvent is evaporated under reduced pressure and the residue is dissolved in an eluent to obtain a sample solution.

(13) In cases where R² is —CH₂CH₂NH₂ and R' is

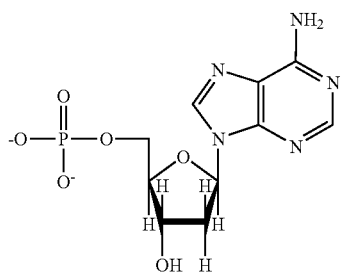

In 50 μL of phosphate buffer (pH7.0), 0.1 to 5.0 μg of a sample is dissolved, and 200 μL of 1 mg/mL probe solution in phosphate buffer (pH7.0) and 1-ethyl-3-(3-dimethylaminopropyl)carbodiimide are added, followed by stirring the resulting mixture at room temperature for 30 minutes. The solvent is evaporated under reduced pressure and the residue is dissolved in an eluent to obtain a sample solution.

The mass spectrometry of a liquid sample using the probe according to the present invention may be carried out in exactly the same manner as ordinary mass spectrometry of a liquid sample after reacting a sample compound and the probe of the present invention so as to bind the probe to the sample compound. The probe according to the present invention may be applied to mass spectrometry of any liquid sample, which accompanies ionization of the sample. Preferred examples of the method for mass spectrometry of liquid samples include electrospray ionization mass spectrometry, atmospheric pressure chemical ionization mass spectrometry, thermospray ionization mass spectrometry, particle beam mass spectrometry and frit fast atom bombardment ionization mass spectrometry, but the method for mass spectrometry is not restricted thereto. Further, the probe may be applied not only to ordinary mass spectrometry, but also to mass spectrometry carried out in an analyzer integral with a reaction bath. For example, the probe according to the present invention may be applied to the mass spectrometry carried out at downstream of a reaction bath or reaction coil in an analyzer in which a reaction bath or reaction coil is incorporated, such as post-column type high performance liquid chromatography apparatus or flow injection analyzer. In this case, the probe is mixed with the sample at upstream of the reaction bath or the reaction coil, and the binding reaction may be carried out in the reaction bath or the reaction coil. The mass spectrometry per se may easily be carried out using a commercially available apparatus, and following the instructions attached to the apparatus.

The term "liquid sample" includes both the sample compound in cases where the sample compound to be analyzed is liquid, and the solution of the sample compound in cases where the sample compound is solid.

In cases where the probe according to the present invention is used, since the sample compound is surely ionized by binding of the probe to the sample compound and since the mass of the moiety in the bound product is known, which moiety is originated from the probe, the sample compound may be quantified with high sensitivity and high accuracy by ordinary mass spectrometry. The molecular weight of the sample compound can be calculated by subtracting the molecular weight of the probe from the observed peak value (m/z value).

The present invention will now be described more concretely by way of examples thereof. It should be noted that the present invention is not limited to the following examples.

EXAMPLE 1

Synthesis of Probe (No. 1)

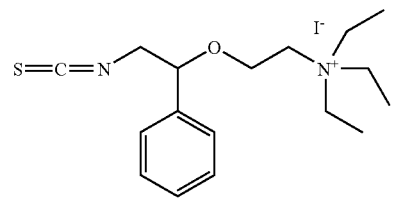

In accordance with the scheme below, the above-described compound having a quaternary amine as R¹ and SCN— as R² was synthesized.

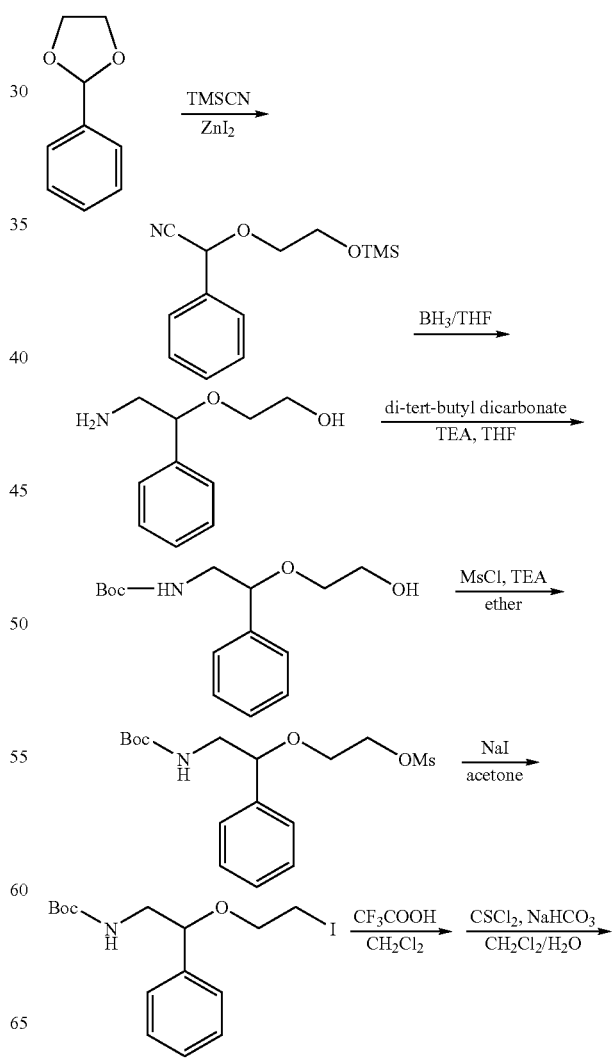

-continued

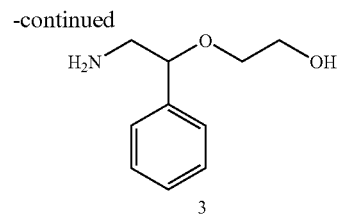

(1) Synthesis of 2-(2-trimethylsiloxyethoxy)-2-phenylethanenitrile

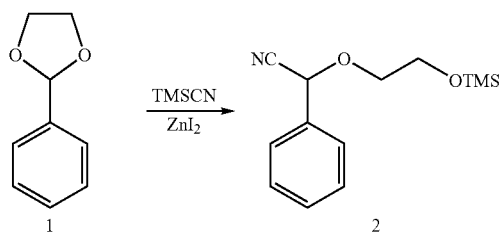

To a 50 ml two-necked flask, 3.0 g (19.9 mmol) of 2-phenyl-1,3-dioxolane (Compound 1), 2.1 ml (21.4 mmol) of trimethylsillyl cyanoide (TMSCN) and 0.3 g (0.94 mmol) of $ZnI_2$ were added and the resulting mixture was stirred under nitrogen gas flow at room temperature for 2 hours. After confirming the disappearance of the materials by TLC ($SiO_2$; $CH_2Cl_2$:n-hexane=1:4 v/v), 100 ml of diethyl ether was added and the resulting mixture was washed with water. The resulting mixture was dried over anhydrous magnesium sulfate and the solvent was evaporated under reduced pressure to obtain a colorless oily product. Identification was carried out using $^1$H-NMR and ESI-TOF mass spectrometry.

Yield: 93% $^1$H-NMR (300 MHz, $CDCl_3$, TMS, r.t., δ/ppm) 0.12 (s, 9H, Si $(CH_3)_3$), 3.65-3.84 (m, 4H, —$OCH_2CH_2O$—), 5.42 (s, 1H, Ar—CH), 7.40-7.58 (m, 5H, ArH) ESI-TOF [M+Na]$^+$=272

(2) Synthesis of 2-(2-amino-1-phenylethoxy)ethane-1-ol

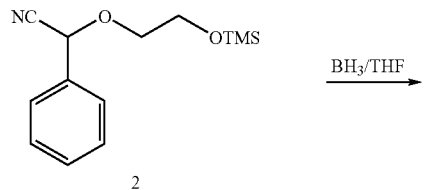

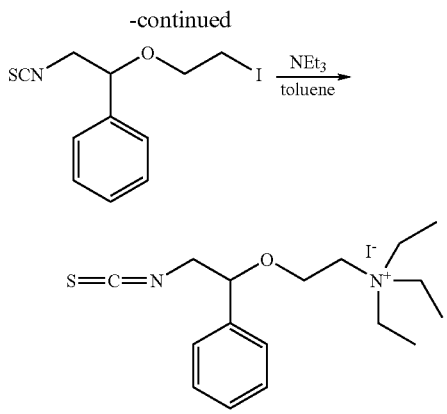

To a 100 ml two-necked flask, 2.0 g (8.0 mmol) of Compound 2 was added and the atmosphere was changed to nitrogen after degassing, followed by adding 50 ml of 1M $BH_3$ solution in THF dropwise for 30 minutes while cooling the mixture in an ice bath. After stirring the mixture at room temperature for 4 hours, disappearance of the materials was confirmed by TLC ($SiO_2$; n-hexane:ethyl acetate=4:1 v/v). To the mixture, 6N HCl was added to make the mixture acidic while cooling the mixture in an ice bath and then most of the solvent was evaporated under reduced pressure. After adding aqueous NaOH solution to adjust the pH to 10, the resulting mixture was extracted three times with 100 ml of ethyl acetate and the organic phase was dried over anhydrous magnesium sulfate. The solvent was evaporated under reduced pressure to obtain a colorless oily product. Identification of the compound was carried out using $^1$H-NMR and ESI-TOF mass spectrometry.

Yield: 90% $^1$H-NMR (300 MHz, $CDCl_3$, TMS, r.t., δ/ppm) 2.55 (br s, 3H), 2.83 (dd, 1H), 3.15 (dd, 1H), 3.39-3.62 (m, 2H), 3.68-3.78 (m, 2H), 5.00 (dd, 1H), 7.40-7.58 (m, 5H) ESI-TOF [M]$^+$=181

(3) Synthesis of (tert-butoxy)-N-(2-(2-hydroxyethoxy)-2-phenylethyl)formamide

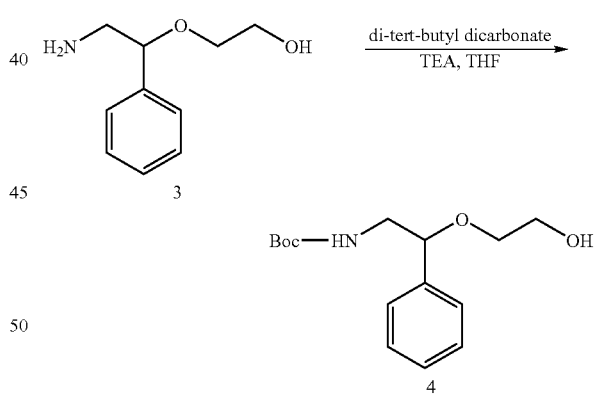

To a 30 ml two-necked flask, 0.50 g (2.76 mmol) of Compound 3 was added and the atmosphere was changed to nitrogen after degassing. Then 15 ml of THF, 0.28 ml (2.76 mmol) of triethylamine and 0.60 g (2.76 mmol) of di-tert-butyl-dicarbonate were added thereto, and the resulting mixture was stirred at room temperature. Two hours later, disappearance of the materials was confirmed by TLC ($SiO_2$; n-hexane:ethyl acetate=1:1), and then the solvent was evaporated under reduced pressure. The product was purified by column chromatography ($SiO_2$; n-hexane:ethyl acetate=1:1) to obtain a colorless oily product. Identification of the compound was carried out using $^1$H-NMR and ESI-TOF mass spectrometry.

Yield: 90% ¹H-NMR (300 MHz, CDCl₃, TMS, r.t., δ/ppm) 1.37 (s, 9H), 3.10 (s, 3H), 3.51-3.64 (m, 4H), 4.33-4.37 (m, 2H), 4.98 (br s, 1H), 5.01 (dd, 1H), 7.41-7.58 (m, 5H) ESI-TOF [M+Na]⁺=304

(4) Synthesis of (tert-butoxy)-N-(2-(2-(methylsulfonyloxy)ethoxy)-2-phenylethylformamide

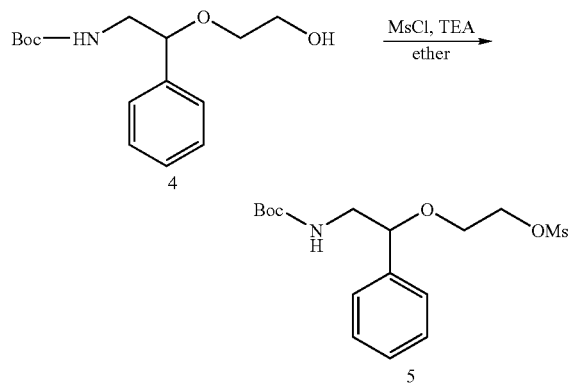

To a 30 ml two-necked flask, 0.50 g (1.78 mmol) of Compound 4 was added and the atmosphere was changed to nitrogen after degassing. Then 10.0 ml of diethyl ether and 0.23 g (2.31 mmol) of triethylamine were added. While cooling the mixture in an ice bath, 0.22 g (1.96 mmol) of methanesulfonyl chloride was added and the resulting mixture was stirred at room temperature. One hour later, disappearance of the materials was confirmed by TLC (SiO₂; n-hexane:ethyl acetate=2:1). After evaporating the solvent under reduced pressure, the product was purified by column chromatography (SiO₂; n-hexane:ethyl acetate=2:1) to obtain white solids. Identification of the compound was carried out using ¹H-NMR and ESI-TOF mass spectrometry.

Yield: 88% ¹H-NMR (300 MHz, CDCl₃, TMS, r.t., δ/ppm) 1.37 (s, 9H), 3.10 (s, 3H), 3.51-3.64 (m, 4H), 4.33-4.37 (m, 2H), 4.98 (br s, 1H), 5.01 (dd, 1H), 7.40-7.58 (m, 5H) ESI-TOF [M+Na]⁺=382

(5) Synthesis of (tert-butoxy)-N-(2-(2-iodoethoxy)-2-phenylethyl)formamide

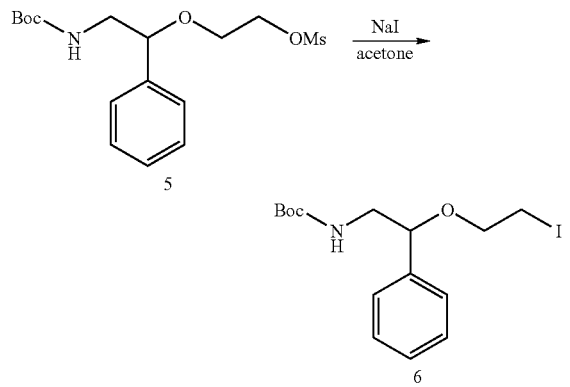

To a 30 ml two-necked flask, 0.50 g (1.39 mmol) of Compound 5 was added and the atmosphere was changed to nitrogen after degassing. Then 10.0 ml of acetone and 1.10 g (7.25 mmol) of sodium iodide were added and the mixture was heated to reflux. Two hours later, disappearance of the materials was confirmed by TLC (SiO₂; n-hexane:ethyl acetate=1:1), and the solvent was evaporated under reduced pressure. The product was purified by column chromatography (SiO₂; n-hexane:ethyl acetate 10:1) to obtain red solids. Identification of the compound was carried out using ¹H-NMR and ESI-TOF mass spectrometry.

Yield: 85% ¹H-NMR (300 MHz, CDCl₃, TMS, r.t., δ/ppm) 1.35 (s, 9H), 3.22 (t, 2H), 3.38-3.66 (m, 4H), 5.02 (br s, 1H), 5.06 (dd, 1H), 7.41-7.58 (m, 5H) ESI-TOF [M+Na]⁺=414

(6) Synthesis of 2-(2-iodoethoxy)-2-phenylethane isothiocyanate

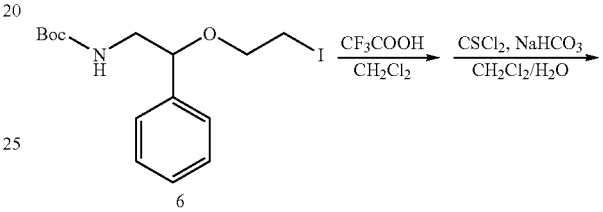

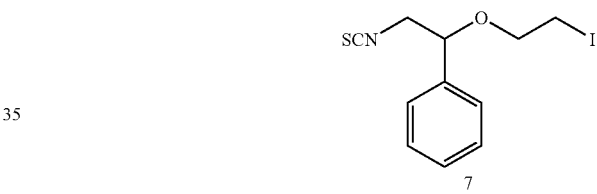

To a 10 ml two-necked flask, 0.20 g (0.51 mmol) of Compound 6 was added and the atmosphere was changed to nitrogen after degassing. Then 2.0 ml of methylene chloride and 0.5 ml of trifluoroacetic acid were added and the resulting mixture was stirred at room temperature. Thirty minutes later, disappearance of the materials was confirmed by TLC (SiO₂; n-hexane:ethyl acetate 4:1), and the solvent was evaporated under reduced pressure. To the obtained compound, 5.0 ml of a mixed solvent of methylene chloride:water=1:1 v/v was added, and then 0.30 g of sodium hydrogen carbonate and 80.0 μl of thiophosgene were added, followed by stirring the mixture at room temperature. One hour later, disappearance of the materials was confirmed by TLC (SiO₂; n-hexane:ethyl acetate=4:1), and the mixture was extracted three times with 50 ml of methylene chloride, followed by drying the organic phase over anhydrous sodium sulfate. The solvent was evaporated under reduced pressure to obtain a yellowish orange oily product. Identification of the compound was carried out using ¹H-NMR and ESI-TOF mass spectrometry.

Yield: 80% ¹H-NMR (300 MHz, CDCl₃, TMS, r.t., δ/ppm) 3.26-3.33 (m, 2H), 3.36-3.79 (m, 2H), 3.80 (dd, 1H), 3.95 (dd, 1H), 5.24 (dd, 1H), 7.40-7.58 (in, 5H) ESI-TOF [M+Na]⁺=355

(7) Synthesis of 2-(2-(triethylamino)ethoxy)-2-phenylethane isothiocyanate iodide

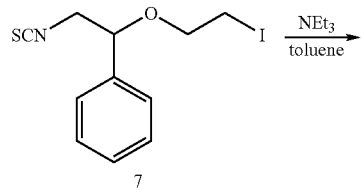

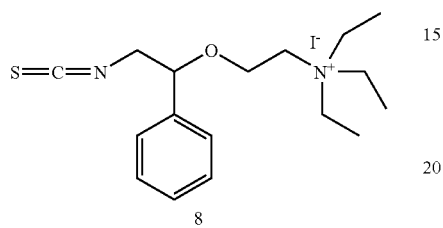

To a 30 ml eggplant type flask, 0.20 g (0.60 mmol) of Compound 7, 5.0 ml of toluene and 1.0 ml of triethylamine were added, and the mixture was stirred at room temperature. Twenty four hours later, disappearance of the materials was confirmed by TLC (SiO$_2$; n-hexane:ethyl acetate=4:1), and the obtained precipitates were recovered, followed by washing the precipitates with toluene to obtain yellowish white solids. Identification of the compound was carried out using $^1$H-NMR and ESI-TOF mass spectrometry.

Yield: 92% $^1$H-NMR (300 MHz, DMSO-d$_6$, TMS, r.t., δ/ppm) 1.30 (t, 9H), 3.04 (q; 6H), 3.75-3.95 (m, 3H), 4.11 (dd, 1H), 4.104.16 (m, 1H), 4.33 (dd, 1H), 5.54 (dd, 1H), 7.40-7.58 (m, 5H) ESI-TOF [M]$^+$=307

EXAMPLE 2

Synthesis of Probe (No. 2)

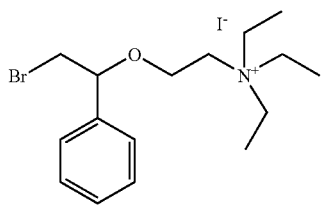

In accordance with the scheme below, the above-described compound having a quaternary amine as R$^1$ and BrH$_2$C— as R$^2$ was synthesized.

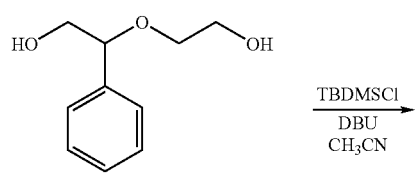

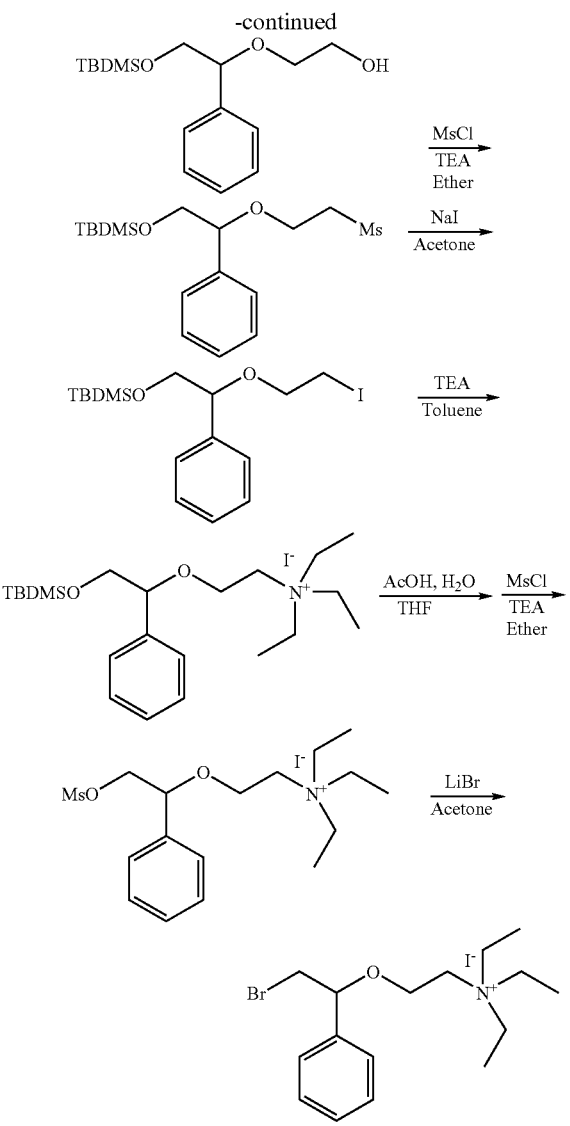

(1) Synthesis of 2-(3,3,4,4-tetramethyl-1-phenyl-3-silapentyloxy)ethane-1-ol

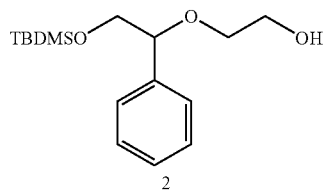

To a 50 ml two-necked flask, 3.0 g (16.5 mmol) of 2-(2-hydroxyethoxy)-2-phenylethane-1-ol (Compound 1), 2.48 g (16.5 mmol) of t-butyldimethylsilyl chloride (TB-DMSCl) and 2.51 ml (16.5 mmol) of 1,8-diazabicyclo[5,4,0]-7-undecene (DBU) were added, and the mixture was stirred under nitrogen gas flow at room temperature for 24 hours. After confirming the disappearance of the materials by TLC, the solvent was evaporated under reduced pressure and the obtained compound was dissolved in methylene chloride. The solution was washed with water and then dried over anhydrous magnesium sulfate. The solvent was evaporated under reduced pressure and the residue was purified by silica gel column chromatography to obtain the desired product.

(2) Synthesis of (methylsulfonyl)oxy (2-(3,3,4,4-tetramethyl-1-phenyl-3-silapentyloxy)ethane

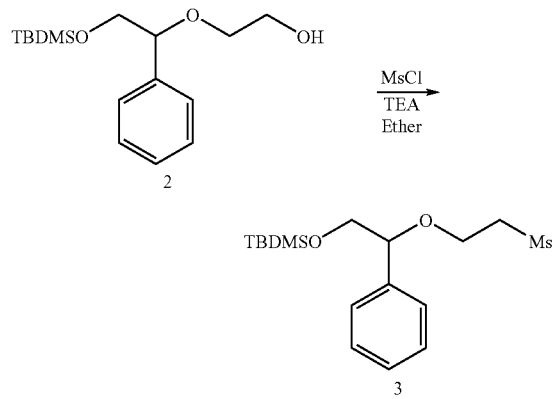

To a 100 ml two-necked flask, 2.0 g (6.75 mmol) of Compound 2 was added and the atmosphere was changed to nitrogen after degassing. Then 20.0 ml of diethyl ether, 0.68 g (6.75 mmol) of triethylamine and 0.77 g (6.75 mmol) of methanesulfonyl chloride were added, and the mixture was stirred at room temperature for 2 hours. The mixture was washed with water and then dried over anhydrous magnesium sulfate. The solvent was evaporated under reduced pressure and the residue was purified by silica gel chromatography to obtain the desired compound.

(3) Synthesis of 2-iodo-1-(3,3,4,4-tetramethyl-1-phenyl-3-silapentyloxy)ethane

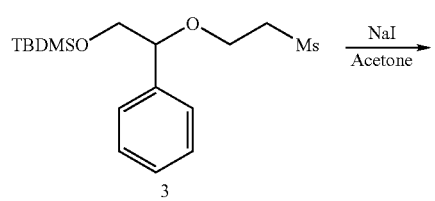

-continued

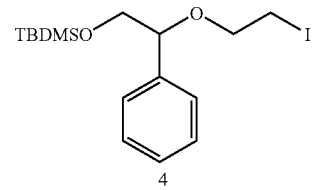

To a 30 ml two-necked flask, 0.50 g (1.25 mmol) of Compound 3 was added and the atmosphere was changed to nitrogen after degassing. Then 15 ml of acetone and 1.49 g (10.0 mmol) of sodium iodide were added and the mixture was heated to reflux for 2 hours. After evaporating the solvent under reduced pressure, the residue was washed with water and dried over anhydrous magnesium sulfate. The solvent was evaporated under reduced pressure and the residue was purified by silica gel column chromatography to obtain the desired compound.

(4) Synthesis of triethyl (2-(3,3,4,4-tetramethyl-1-phenyl-3-silapentyloxy)ethyl)amine

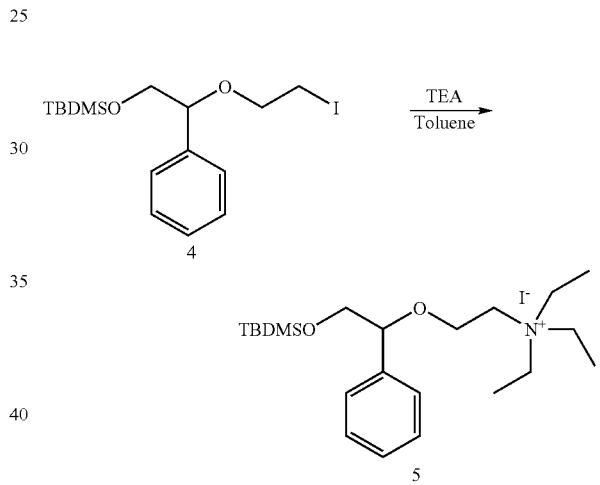

To a 30 ml eggplant type flask, 0.50 g (1.25 mmol) of Compound 4, 10.0 ml of toluene and 1.0 ml of triethylamine were added, and the mixture was stirred at room temperature for 24 hours. The obtained precipitates were recovered and washed with toluene, followed by drying under reduced pressure to obtain the desired compound.

(5) Synthesis of 1-(methylsulfonyl)-2-phenyl-2-(2-(triethylamino)ethoxy)ethane

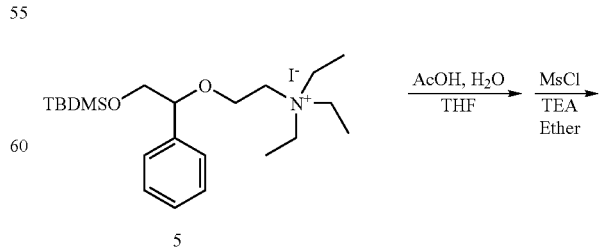

-continued

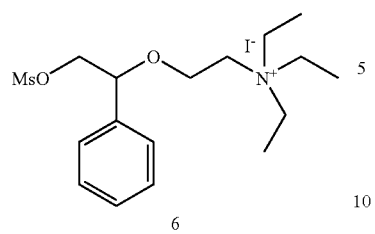

6

To a 30 ml two-necked flask, 0.50 g (1.37 mmol) of Compound 5 and 10.0 ml of a mixed solvent of acetic acid:water:THF=3:1:1 v/v were added and the mixture was stirred at room temperature for 2 hours. The solvent was evaporated under reduced pressure and the resultant was dried under reduced pressure using a pump. To the obtained compound, 10.0 ml of diethyl ether, triethylamine and methanesulfonyl chloride were added and the resulting mixture was stirred at room temperature for 2 hours. The mixture was washed with water and then dried over anhydrous magnesium sulfate. The solvent was evaporated and the residue was purified by silica gel column chromatography to obtain the obtained compound.

(6) Synthesis of (2-(2-iodo-1-phenylethoxy)ethyl)triethylamine

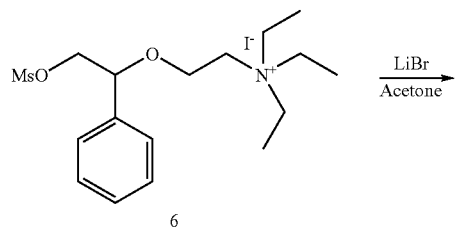

6

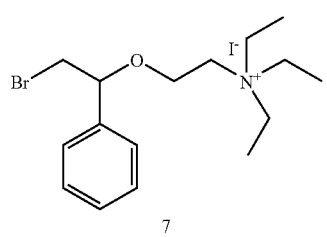

7

To a 50 ml eggplant type flask, 0.20 g (0.58 mmol) of Compound 6, 20.0 ml of acetone and 0.43 g (5.0 mmol) of lithium bromide were added and the mixture was heated to reflux for 2 hours. The solvent was evaporated under reduced pressure and ethanol was added. Insoluble materials were removed by filtration and the filtrate was concentrated under reduced pressure to obtain the desired compound.

EXAMPLE 3

Synthesis of Probe (No. 3)

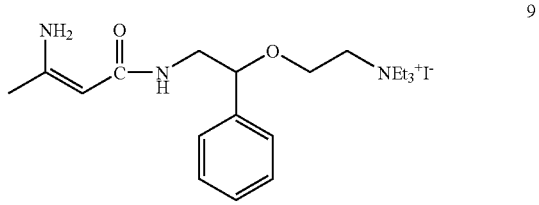

9

In accordance with the scheme below, the above-described compound having a quaternary amine as $R^1$ and $NH_2$— as $R^2$ was synthesized.

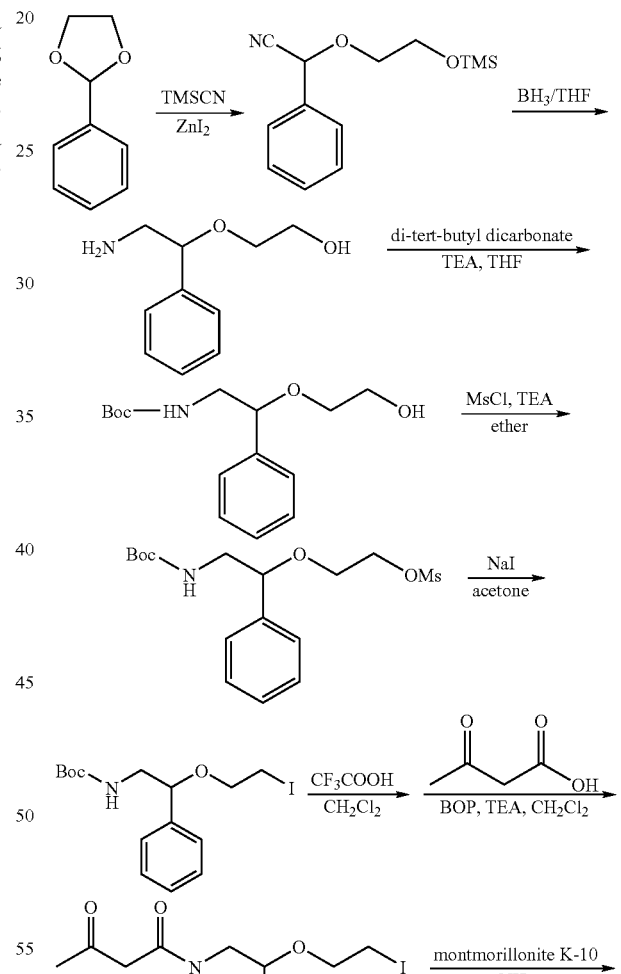

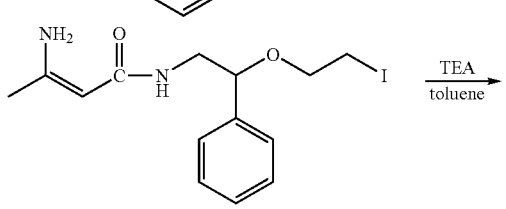

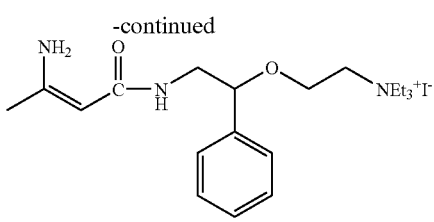

(1) Synthesis of 2-(2-trimethylsiloxyethoxy)-2-phenylethanenitrile

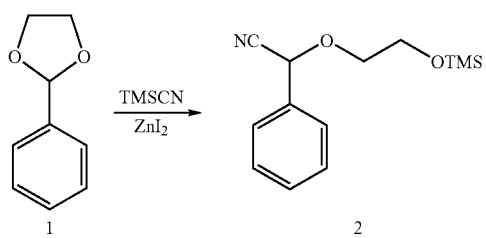

To a 50 ml two-necked flask, 3.0 g (19.9 mmol) of 2-phenyl-1,3-dioxolane (Compound 1), 2.1 ml (21.4 mmol) of TMSCN and 0.3 g (0.94 mmol) of $ZnI_2$ were added and the mixture was stirred under nitrogen gas flow at room temperature for 2 hours. After confirming the disappearance of the materials by TLC ($SiO_2$; $CH_2Cl_2$:n-hexane=1:4 v/v), 100 ml of diethyl ether was added and the resulting mixture was washed with water. The mixture was dried over anhydrous magnesium sulfate and the solvent was evaporated under reduced pressure to obtain a colorless oily compound. Identification of the compound was carried out using $^1$H-NMR and ESI-TOF mass spectrometry.

Yield: 93% $^1$H-NMR (300 MHz, $CDCl_3$, TMS, r.t., δ/ppm) 0.12 (s, 9H, Si $(CH_3)_3$), 3.65-3.84 (m, 4H, —OCH2CH$_2$O—), 5.42 (s, 1H, Ar—CH), 7.40-7.58 (m, 5H, ArH) ESI-TOF [M+Na]$^+$=272

(2) Synthesis of 2-(2-amino-1-phenylethoxy)ethane-1-ol

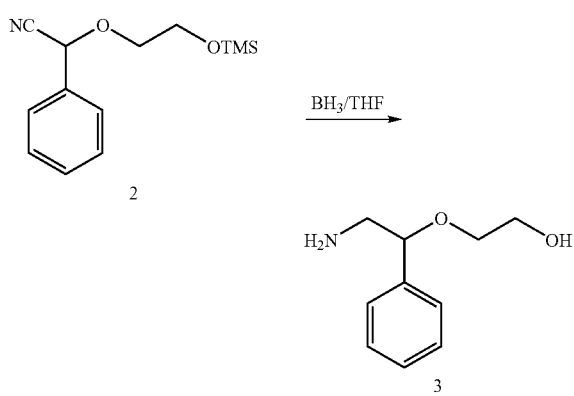

To a 100 ml two-necked flask, 2.0 g (8.0 mmol) of Compound 2 was added and the atmosphere was changed to nitrogen after degassing, followed by adding 50 ml of 1M $BH_3$ solution in THF dropwise for 30 minutes while cooling the mixture in an ice bath. After stirring the mixture at room temperature for 4 hours, disappearance of the materials was confirmed by TLC ($SiO_2$; n-hexane:ethyl acetate=4:1 v/v). To the mixture, 6N HCl was added to make the mixture acidic while cooling the mixture in an ice bath and then most of the solvent was evaporated under reduced pressure. After adding aqueous NaOH solution to adjust the pH to 10, the resulting mixture was extracted three times with 100 ml of ethyl acetate and the organic phase was dried over anhydrous magnesium sulfate. The solvent was evaporated under reduced pressure to obtain a colorless oily product. Identification of the compound was carried out using $^1$H-NMR and ESI-TOF mass spectrometry.

Yield: 90% $^1$H-NMR (300 MHz, $CDCl_3$, TMS, r.t., δ/ppm) 2.55 (br s, 3H), 2.83 (dd, 1H), 3.15 (dd, 1H), 3.39-3.62 (m, 2H), 3.68-3.78 (m, 2H), 5.00 (dd, 1H), 7.40-7.58 (m, 5H) ESI-TOF [M]$^+$=181

(3) Synthesis of (tert-butoxy)-N-(2-(2-hydroxyethoxy)-2-phenylethyl)formamide

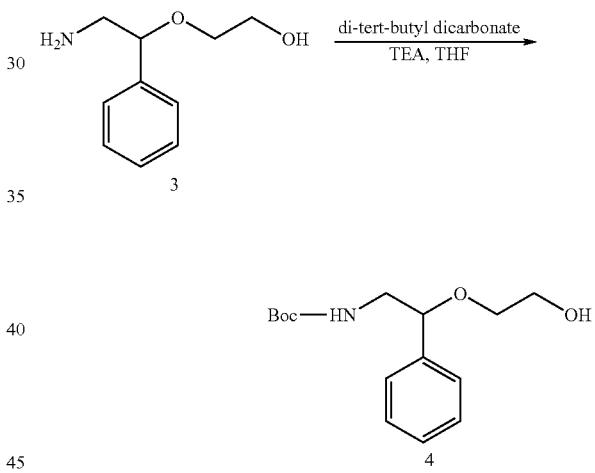

To a 30 ml two-necked flask, 0.50 g (2.76 mmol) of Compound 3 was added and the atmosphere was changed to nitrogen after degassing. Then 15 ml of THF, 0.28 ml (2.76 mmol) of triethylamine, 0.60 g (2.76 mmol) of di-tert-butyl-dicarbonate were added thereto, and the resulting mixture was stirred at room temperature. Two hours later, disappearance of the materials was confirmed by TLC ($SiO_2$; n-hexane:ethyl acetate=1:1), and then the solvent was evaporated under reduced pressure. The product was purified by column chromatography ($SiO_2$; n-hexane:ethyl acetate=1:1) to obtain a colorless oily product. Identification of the compound was carried out using $^1$H-NMR and ESI-TOF mass spectrometry.

Yield: 90% $^1$H-NMR (300 MHz, $CDCl_3$, TMS, r.t., δ/ppm) 1.37 (s, 9H), 3.10 (s, 3H), 3.51-3.64 (m, 4H), 4.33-4.37 (m, 2H), 4.98 (br s, 1H), 5.01 (dd, 1H), 7.41-7.58 (m, 5H) ESI-TOF [M+Na]$^+$=304

(4) Synthesis of (tert-butoxy)-N-(2-(2-(methylsulfonyloxy)ethoxy)-2-phenylethylformamide

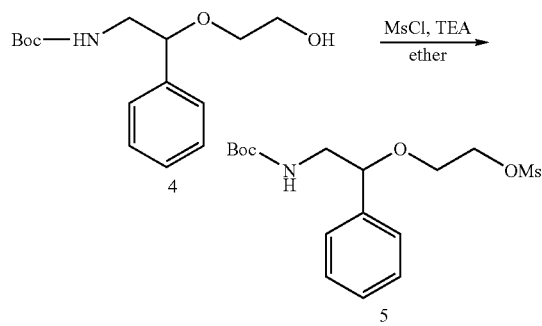

To a 30 ml two-necked flask, 0.50 g (1.78 mmol) of Compound 4 was added and the atmosphere was changed to nitrogen after degassing. Then 10.0 ml of diethyl ether and 0.23 g (2.31 mmol) of triethylamine were added. While cooling the mixture in an ice bath, 0.22 g (1.96 mmol) of methanesulfonyl chloride was added and the resulting mixture was stirred at room temperature. One hour later, disappearance of the materials was confirmed by TLC (SiO$_2$; n-hexane:ethyl acetate=2:1). After evaporating the solvent under reduced pressure, the product was purified by column chromatography (SiO$_2$; n-hexane:ethyl acetate=2:1) to obtain white solids. Identification of the compound was carried out using $^1$H-NMR and ESI-TOF mass spectrometry.

Yield: 88% $^1$H-NMR (300 MHz, CDCl$_3$, TMS, r.t., δ/ppm) 1.37 (s, 9H), 3.10 (s, 3H), 3.51-3.64 (m, 4H), 4.33-4.37 (m, 2H), 4.98 (br s, 1H), 5.01 (dd, 1H), 7.40-7.58 (m, 5H) ESI-TOF [M+Na]$^+$=382

(5) Synthesis of (tert-butoxy)-N-(2-(2-iodoethoxy)-2-phenylethyl)formamide

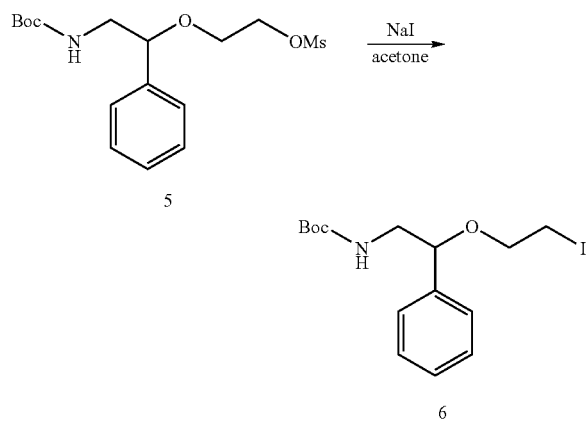

To a 30 ml two-necked flask, 0.50 g (1.39 mmol) of Compound 5 was added and the atmosphere was changed to nitrogen after degassing. Then 10.0 ml of acetone and 1.10 g (7.25 mmol) of sodium iodide were added and the mixture was heated to reflux. Two hours later, disappearance of the materials was confirmed by TLC (SiO$_2$; n-hexahe:ethyl acetate 1:1), and the solvent was evaporated under reduced pressure. The product was purified by column chromatography (SiO$_2$; n-hexane:ethyl acetate=10:1) to obtain red solids. Identification of the compound was carried out using $^1$H-NMR and ESI-TOF mass spectrometry.

Yield: 85%. $^1$H-NMR (300 MHz, CDCl$_3$, TMS, r.t., δ/ppm) 1.35 (s, 9H), 3.22 (t, 2H), 3.38-3.66 (m, 4H), 5.02 (br s, 1H), 5.06 (dd, 1H), 7.41-7.58 (m, 5H) ESI-TOF [M+Na]$^+$ =414

(6) Synthesis of N-(2-(2-iodoethoxy)-2-phenylethyl)-3-oxobutaneamide

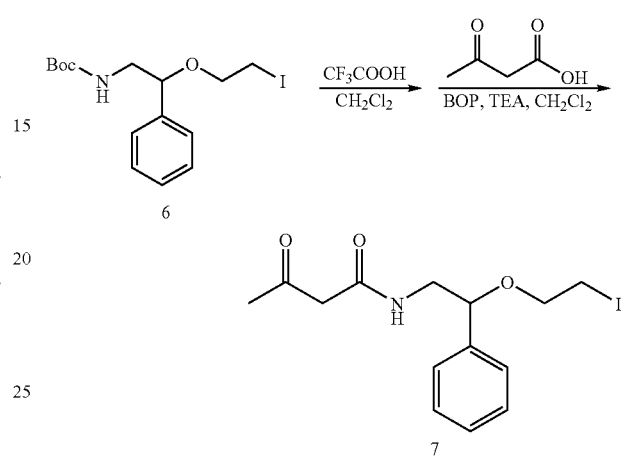

To a 10 ml two-necked flask, 0.20 g (0.51 mmol) of Compound 6 was added and the atmosphere was changed to nitrogen after degassing. Then 2.0 ml of methylene chloride and 0.5 ml of trifluoroacetic acid were added, and the mixture was stirred at room temperature. Thirty minutes later, disappearance of the materials was confirmed by TLC (SiO$_2$; n-hexane:ethyl acetate=4:1), and the solvent was evaporated under reduced pressure. To the obtained compound, 5.0 ml of methylene chloride, 0.05 g (0.51 mmol) of trimethylamrine and 0.05 g (0.51 mmol) of acetoacetic acid were added, and the mixture was stirred for 30 minutes while cooling the mixture in an ice bath. After adding 0.22 g (0.51 mmol) of BOP(Benzotriazol-1-yloxytris(dimethylamino)phosphonium hexafluorophosphate) reagent, the mixture was stirred for 30 minutes while cooling the mixture in an ice bath and then for 24 hours at room temperature. Disappearance of the materials was confirmed by TLC (SiO$_2$; n-hexane:ethyl acetate=4:1), and the mixture was extracted three times with 50 ml of methylene chloride and the organic phase was dried over anhydrous magnesium sulfate. The solvent was evaporated under reduced pressure to obtain the compound.

(7) Synthesis of 3-amino-N-(2-(2-iodoethoxy)-2-phenylethyl)-2-buteneamide

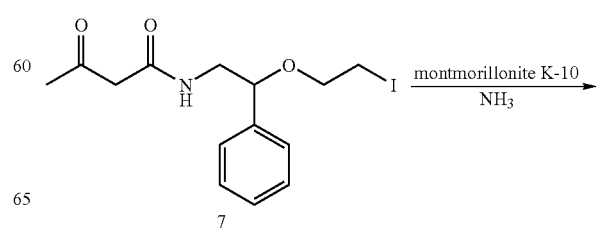

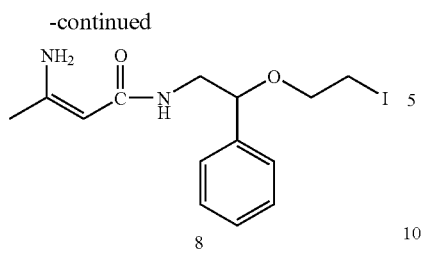

8

To a 10 ml eggplant type flask, 0.20 g (0.60 mmol) of Compound 7, 5.0 ml of aqueous ammonia and 0.1 g of montmorillonite K-10 were added, and the mixture was stirred for 24 hours at room temperature. After extracting the mixture with methylene chloride, the organic phase was washed with water and dried over anhydrous magnesium sulfate. The solvent was evaporated under reduced pressure and the residue was purified by silica gel column chromatography.

(8) Synthesis of 3-amino-N-(2-phenyl-2-(2-(triethylamino)ethoxy)ethyl)-2-buteneamide

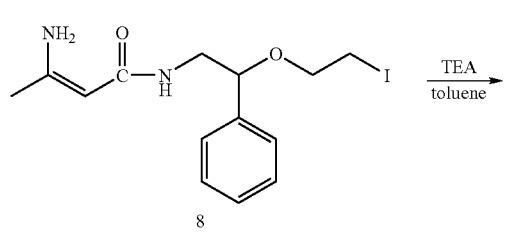

8

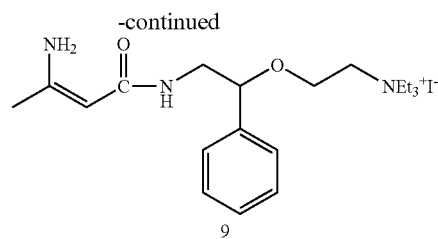

9

To a 10 ml eggplant type flask, 0.20 g (0.58 mmol) of Compound 8, 5.0 ml of toluene and 1.0 ml of triethylamine were added, and the mixture was stirred at room temperature for 24 hours. The generated precipitates were recovered and washed with toluene, followed by drying under reduced pressure.

EXAMPLE 4

Synthesis of Probe (No. 4)

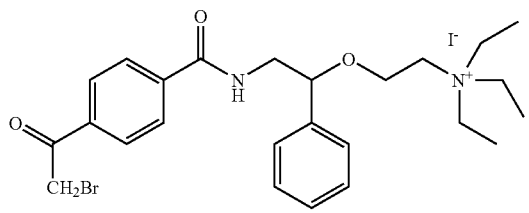

8

In accordance with the scheme below, the above-described compound having a quaternary amine as $R^1$ and —COCH$_2$Br as $R^2$ was synthesized.

Scheme

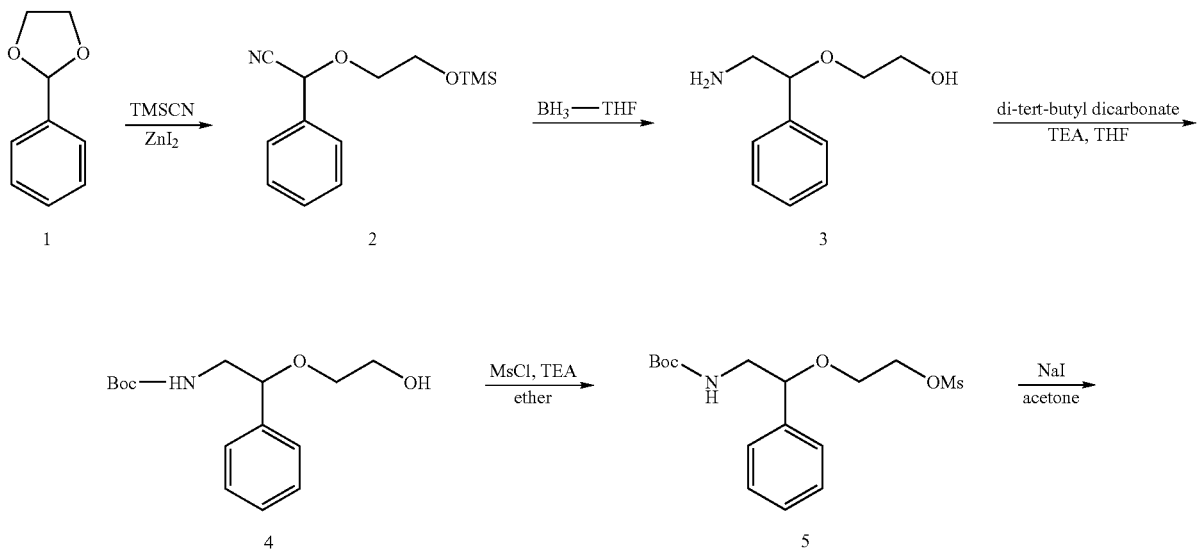

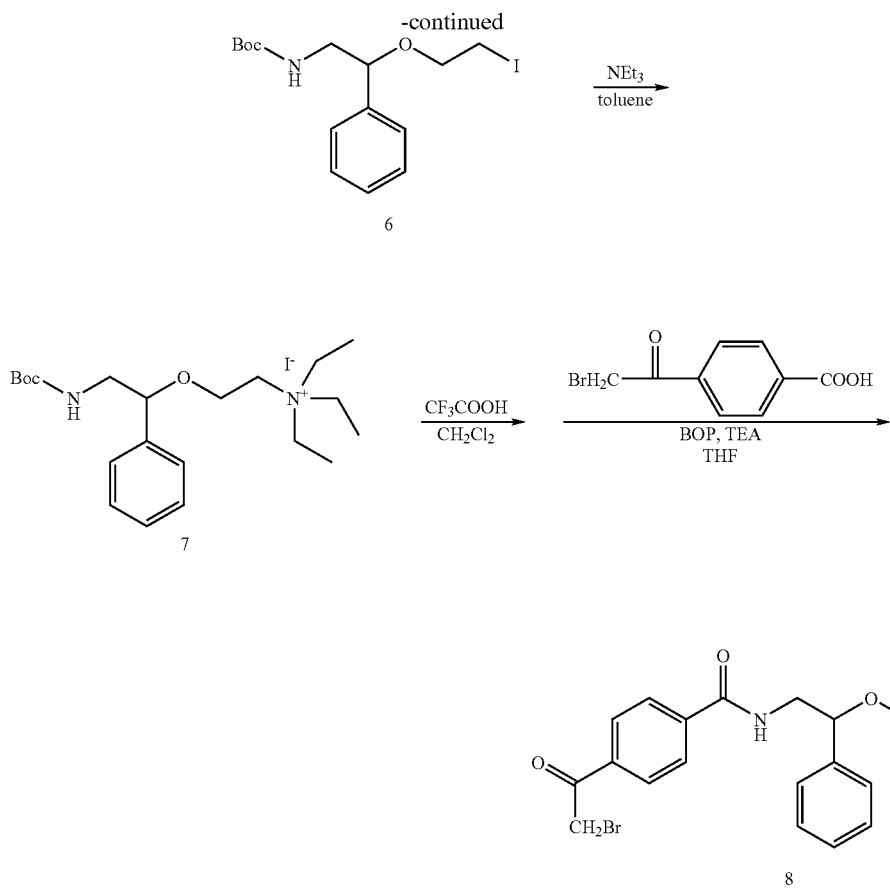

(1) Synthesis of phenyl-(2-trimethylsilanyloxy-ethoxy)-acetonitrile (Compound 2)

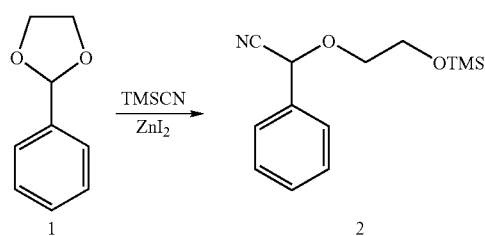

To a 30 ml eggplant type flask, 3.0 g (19.9 mmol) of 2-phenyl-1,3-pentadione (Compound 1) was added and the flask was dipped in an ice bath. To the flask, 2.1 ml (21.43 mmol) of TMSCN and 0.3 g (0.94 mmol) of $ZnI_2$ were added, and the mixture was stirred at room temperature for 2 hours. Diethyl ether was added to the reaction solution and the mixture was washed with water, followed by drying using $MgSO_4$. The solvent was evaporated under reduced pressure to obtain a yellow oily product (4.17 g, yield: 83.2%).

$^1$H-NMR (270 MHz, $CDCl_3$, TMS, r.t., δ/ppm) 0.15(s, 9H, $SiCH_3$), 3.80(t, 2H, —$OCH_2CH_2OSi$—), 4.11(t, 2H, —$OCH_2CH_2OSi$—), 5.39(s, 1H, ARCH), 7.45(m, 5H, ArH) ESI-TOF(+): [M+Na]$^+$272.0

(2) Synthesis of 2-(2-amino-1-phenyl-ethoxy)-ethanol (Compound 3)

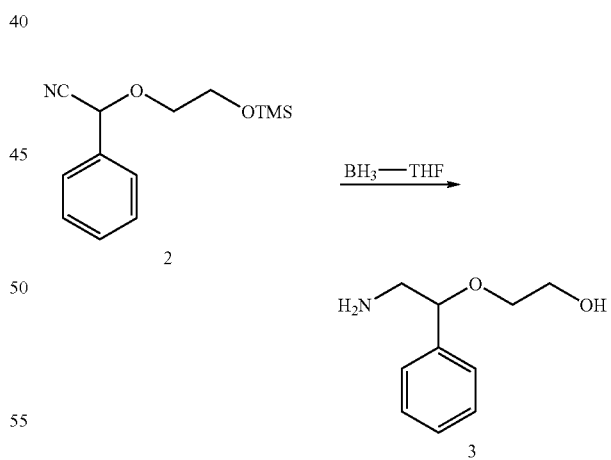

To a 100 ml three-necked flask, 1.0 g (4.01 mmol) of Compound 2 was added and the atmosphere was changed to nitrogen after degassing. The flask was-dipped in an ice bath and 30 ml of 1M $BH_3$ solution in THF was slowly added. The resulting mixture was stirred for 30 minutes while cooling the mixture in ice and then at room temperature for 4 hours. After completion of the reaction, the reaction vessel was dipped in an ice bath and aqueous 1N HCl solution was added, thereby making the mixture acidic. After evaporating the solvent under reduced pressure, 20 ml of water was added and aqueous NaOH solution was added to adjust the pH to 10. The mixture was extracted with ethyl acetate and the organic phase was washed with water, followed by drying over anhydrous sodium sulfate to obtain a colorless oily compound (650 mg, Yield: 89.5,%).

$^1$H-NMR (300 MHz, CDCl$_3$, TMS, r.t., δ/ppm) 2.95(d, 2H, NH$_2$—CH$_2$), 3.65(t, 2H, —OCH$_2$CH$_2$OH), 3.75(t, 2H, —OCH$_2$CH$_2$OH), 4.46(t, 1H, ARCH), 7.32(m, 5H, ArH) ESI-TOF (+): [M+H]$^+$=182.0

(3) Synthesis of [2-(2-hydroxy-ethoxy)-2-phenyl-ethyl]-carbamic acid tert-butyl ester

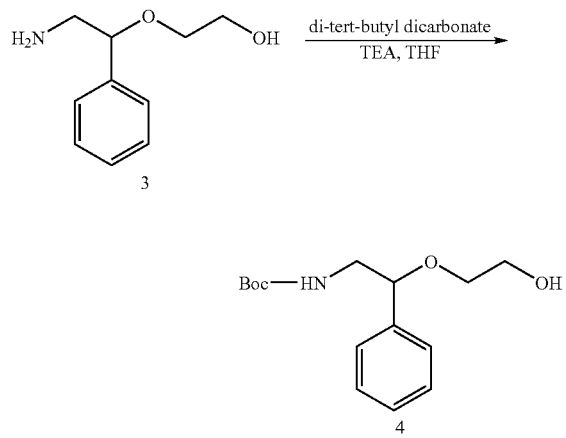

To a 100 ml two-necked flask, 1.40 g (7.70 mmol) of Compound 3 was added and the atmosphere was changed to nitrogen. While cooling the flask in an ice bath, 55 ml of anhydrous THF, 0.78 g (7.69 mmol) of TEA and 1.68 g (7.70 mmol) of di-tert-butyl-dicarbonate were added, and the mixture was stirred at room temperature for 2 hours. The solvent was evaporated under reduced pressure and the residue was purified by column chromatography (SiO$_2$, chloroform) to obtain a yellow oily compound (1.30 g, Yield: 59.9%).

$^1$H-NMR (300 MHz, CDCl$_3$, TMS, r.t., δ/ppm) 1.48(s, 9H, t-Bu), 3.24(d, 2H, NH—CH$_3$), 3.49(t, 2H, —OCH$_2$CH$_2$OH), 3.73(t, 2H, —OCH$_2$CH$_2$OH), 4.42(t, 1H, ArCH), 7.33(m, 5H, ArH) ESI-TOF (+): [M+Na]$^+$=304.0

(4) Synthesis of methanesulfonic acid 2-(2-tert-butoxycarbonylamino-1-phenyl-ethoxy) ethyl ester (Compound 5)

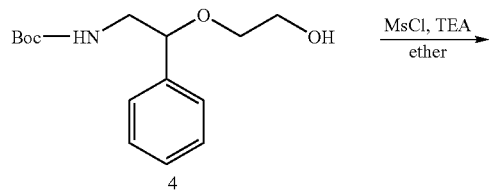

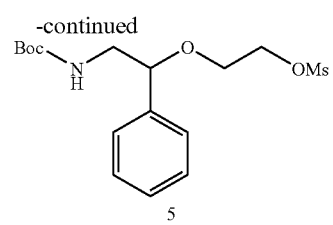

To a 50 ml eggplant type flask, 500 mg (1.78 mmol) of Compound 4 was added and the atmosphere was changed to nitrogen. Then 16 ml of anhydrous THF and 0.5 ml (4.55 mmol) of TEA were added and the flask was dipped in an ice bath. To the mixture, 440 mg (3.84 mmol) of MsCl was added and the resulting mixture was stirred at room temperature for 1 hour. After evaporating the solvent under reduced pressure, chloroform was added and the generated precipitates were removed by filtration, followed by concentrating the filtrate under reduced pressure. The resulting product was purified by column chromatography (SiO$_2$, ethyl acetate: n-hexane=2:1 v/v) to obtain a yellow oily product (491 mg, Yield: 77.0%).

$^1$H-NMR (300 MHz, CDCl$_3$, TMS, r.t., δ/ppm) 1.44(s, 9H, t-Bu), 3.24(d, 2H, NH—CH$_2$), 3.44(t, 2H, —OCH$_2$CH$_2$OS—), 3.62(t, 2H, —OCH$_2$CH$_2$OS—), 4.34(t, 1H, ArCH), 7.33(m, 5H, ArH) ESI-TOF (+): [M+Na]$^+$=382.2

(5) Synthesis of [2-(2-iodo-ethoxy)-2-phenyl-ethyl]-carbamic acid tert-butyl ester (Compound-6)

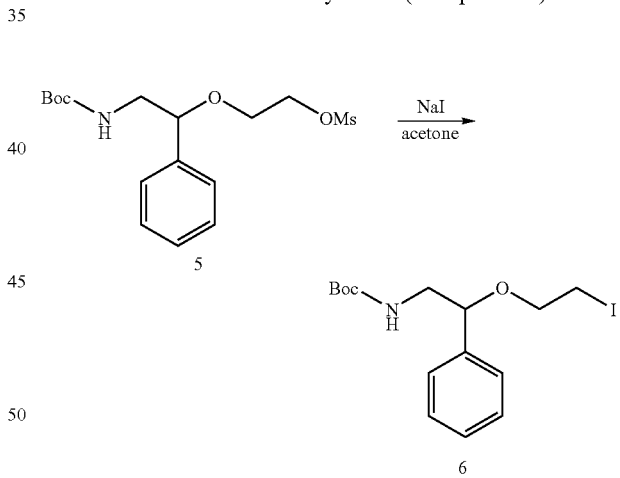

To a 50 ml eggplant type flask, 100 mg (0.28 mmol) of Compound 5 was added and the atmosphere was changed to nitrogen. Then 10 ml of acetone and 10.0 g (6.67 mmol) of NaI were added, and the mixture was heated to reflux for 2 hours. After removing NaI by filtration, the solvent was evaporated under reduced pressure. The residue was purified by column chromatography (SiO$_2$, n-hexane:ethyl acetate=1:1 v/v) to obtain a yellow oily compound (104 mg, Yield: 93.99%).

$^1$H-NMR (270 MHz, CDCl$_3$, TMS, r.t., δ/ppm) 1.45(s, 9H, t-Bu), 3.22(t, 2H, I—CH$_2$), 3.49(d, 2H, NH—CH$_2$), 3.67(t, 2H, —OCH$_2$), 4.43(t, 1H, ArCH), 7.34(m, 5H, ArH) ESI-TOF (+): [M+Na]$^+$=413.9

(6) Synthesis of [2-(2-tert-butoxycarbonylamino-1-phenyl-ethoxy)-ethyl]-triethyl-ammonium iodide (Compound 2)

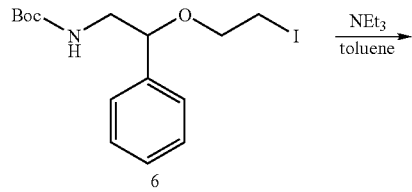

6

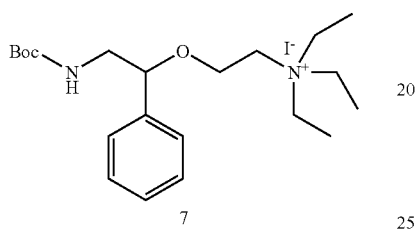

7

To a 50 ml eggplant type flask, 350 mg (0.90 mmol) of Compound 6, 8.75 ml of toluene and 1.75 ml (17.33 mmol) of TEA were added, and the reaction was carried out at 80° C. for 24 hours. After evaporating the solvent under reduced pressure, the residue was purified by large thin layer chromatography (SiO$_2$, chloroform:methanol=7:1 v/v) to obtain a reddish yellow solid product (383 mg, Yield: 66.70%). $^1$H-NMR (300 MHz, CDCl$_3$, TMS, r.t., δ/ppm) 1.42(t, 9H, CH$_2$—CH$_3$), 1.48(s, 9H, t-Bu), 3.53(q, 6H, NR$_3$—CH$_2$), 3.70(t, 2H, —OCH$_2$CH$_2$N—), 3.72(d, 2H, NH—CH$_2$), 3.95(t, 2H, —OCH$_2$CH$_2$N—), 4.63(t, 1H, ArCH), 7.35(m, 5H, ArH) ESI-TOF (+): [M]$^+$365.2

(7) Synthesis of Compound 8

To a 30 ml eggplant type flask, 0.50 g (1.02 mmol) of Compound 7, 0.50 ml of TFA (trifluoroacetic acid) and 10.0 ml of methylene chloride were added, and the mixture was stirred at room temperature for 30-minutes. The solvent was evaporated under reduced pressure and the resultant was dried under reduced pressure using a pump. After changing the atmosphere to nitrogen, 20.0 ml of THF, 0.10 g (1.02 mmol) of TEA, 0.10 g (1.02 mmol) of BOP and 0.25 g (1.02 mmol) of 4-bromomethylacetyl benzoic acid were added, and the mixture was stirred at room temperature for 24 hours. After evaporating the solvent under reduced pressure, the residue was purified by column chromatography to obtain the desired compound.

EXAMPLE 5

Synthesis of Probe (No. 5)

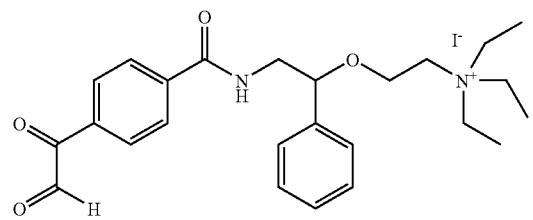

9

In accordance with the scheme below, the above-described compound having a quaternary amine as R$^1$ and —COCHO as R$^2$ was synthesized.

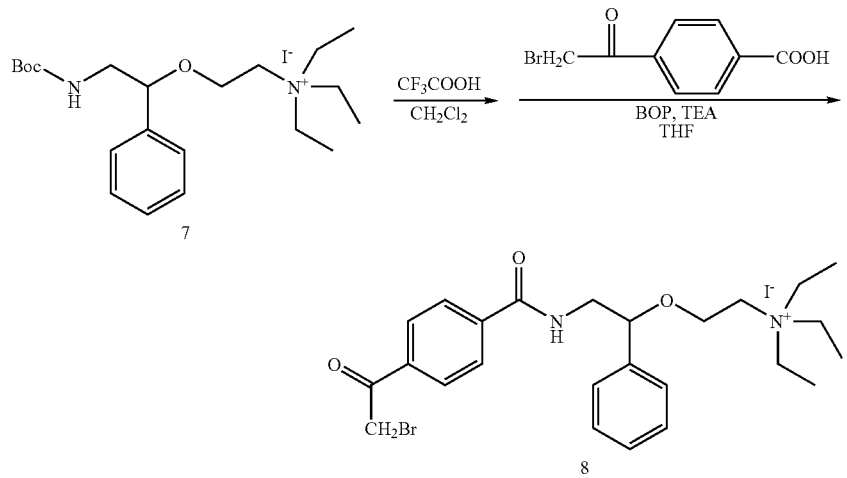

8

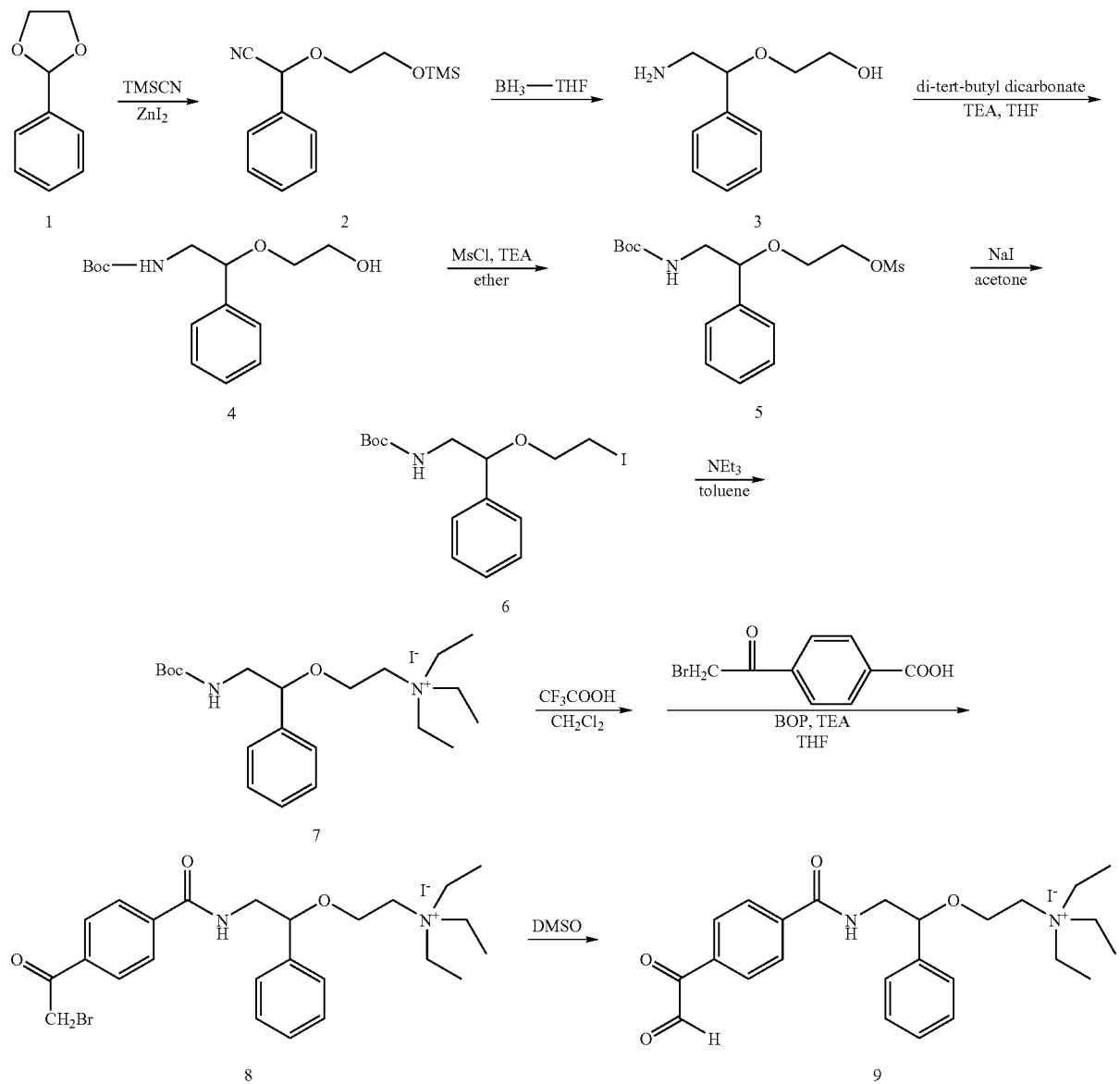

(1) Synthesis of
phenyl-(2-trimethylsilanyloxy-ethoxy)-acetonitrile
(Compound 2)

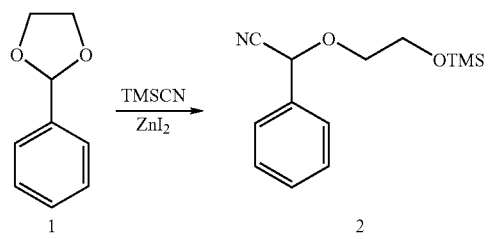

To a 30 ml eggplant type flask, 3.0 g (19.9 mmol) of 2-phenyl-1,3-pentadione (Compound 1) was added and the flask was dipped in an ice bath. To the flask, 2.1 ml (21.43 mmol) of TMSCN and 0.3 g (0.94 mmol) of $ZnI_2$ were added, and the mixture was stirred at room temperature for 2 hours. Diethyl ether was added to the reaction solution and the mixture was washed with water, followed by drying using $MgSO_4$. The solvent was evaporated under reduced pressure to obtain a yellow oily product (4.17 g, yield: 83.2%).

$^1$H-NMR (270 MHz, $CDCl_3$, TMS, r.t., δ/ppm) 0.15(s, 9H, $SiCH_3$), 3.80(t, 2H, —$OCH_2CH_2OSi$—), 4.11(t, 2H, —$OCH_2CH_2OSi$—), 5.39(s, 1H, ArCH), 7.45(m, 5H, ArH) ESI-TOF (+): [M+Na]$^+$=272.0-

(2) Synthesis of 2-(2-amino-1-phenyl-ethoxy)-ethanol (Compound 3)

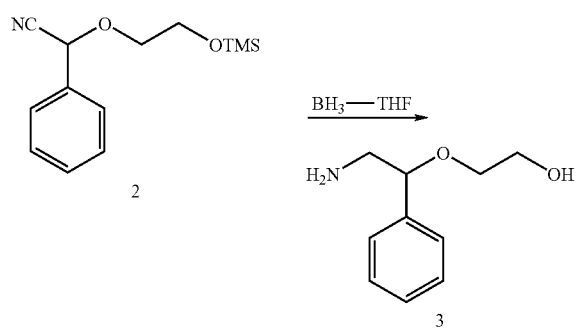

To a 100 ml three-necked flask, 1.0 g (4.01 mmol) of Compound 2 was added and the atmosphere was changed to nitrogen after degassing. The flask was dipped in an ice bath and 30 ml of 1M $BH_3$ solution in THF was slowly added. The resulting mixture was stirred for 30 minutes while cooling the mixture in ice and then at room temperature for 4 hours. After completion of the reaction, the reaction vessel was dipped in an ice bath and aqueous 1N HCl solution was added, thereby making the mixture acidic. After evaporating the solvent under reduced pressure, 20 ml of water was added and aqueous NaOH solution was added to adjust the pH to 10. The mixture was extracted with ethyl acetate and the organic phase was washed with water, followed by drying over anhydrous sodium sulfate to obtain a colorless oily compound (650 mg, Yield: 89.5%).

$^1$H-NMR (300 MHz, $CDCl_3$, TMS, r.t., δ/ppm) 2.95(d, 2H, $NH_2$—$CH_2$), 3.65(t, 2H, —$OCH_2CH_2OH$), 3.75(t, 2H, —$OCH_2CH_2OH$), 4.46(t, 1H, ArCH), 7.32(m, 5H, ArH)

ESI-TOF (+): $[M+H]^+$=182.0

(3) Synthesis of [2-(2-hydroxy-ethoxy)-2-phenyl-ethyl]-carbamic acid tert-butyl ester (Compound 4)

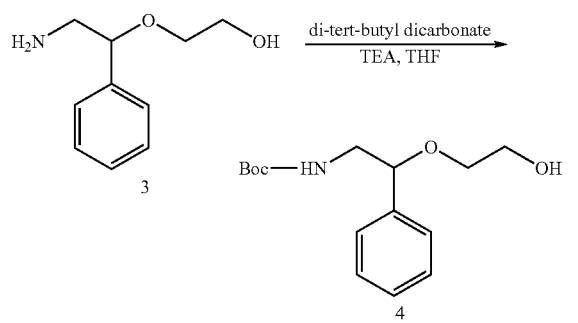

To a 100 ml two-necked flask, 1.40 g (7.70 mmol) of Compound 3 was added and the atmosphere was changed to nitrogen. While cooling the flask in an ice bath, 55 ml of anhydrous THF, 0.78 g (7.69 mmol) of TEA and 1.68 g (7.70 mmol) of di-tert-butyl-dicarbonate were added, and the mixture was stirred at room temperature for 2 hours. The solvent was evaporated under reduced pressure and the residue was purified by column chromatography ($SiO_2$, chloroform) to obtain a yellow oily, compound (1.30 g, Yield: 59.9%).

$^1$H-NMR (300 MHz, $CDCl_3$, TMS, r.t., δ/ppm) 1.48(s, 9H, t-Bu), 3.24(d, 2H, NH—$CH_3$), 3.49(t, 2H, —$OCH_2CH_2OH$), 3.73(t, 2H, —$OCH_2CH_2OH$), 4.42(t, 1H, ArCH), 7.33(m, 5H, ArH)

ESI-TOF (+): $[M+Na]^+$=304.0

(4) Synthesis of methanesulfonic acid 2-(2-tert-butoxycarbonylamino-1-phenyl-ethoxy) ethyl ester (Compound 5)

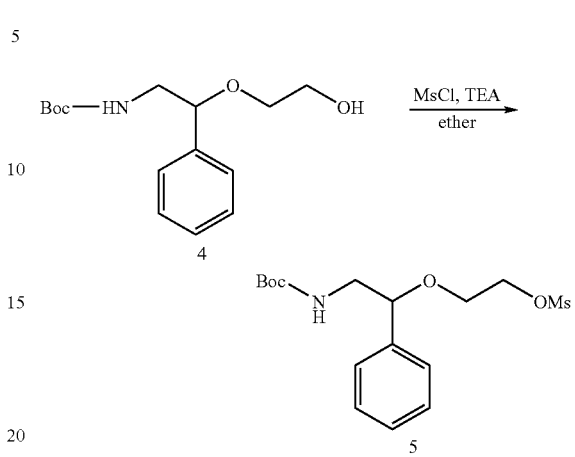

To a 50 ml eggplant type flask, 500 mg (1.78 mmol) of Compound 4 was added and the atmosphere was changed to nitrogen. Then 16 ml of anhydrous THF and 0.5 ml (4.55 mmol) of TEA were added and the flask was dipped in an ice bath. To the mixture, 440 mg (3.84 mmol) of MsCl was added and the resulting mixture was stirred at room temperature for 1 hour. After evaporating the solvent under reduced pressure, chloroform was added and the generated precipitates were removed by filtration, followed by concentrating the filtrate under reduced pressure. The resulting product was purified by column chromatography ($SiO_2$, ethyl acetate: n-hexane=2:1 v/v) to obtain a yellow oily product (491 mg, Yield: 77.0%).

$^1$H-NMR (300 MHz, $CDCl_3$, TMS, r.t., δ/ppm) 1.44(s, 9H, t-Bu), 3.24(d, 2H, NH—$CH_2$), 3.44(t, 2H, —$OCH_2CH_2OS$—), 3.62(t, 2H, —$OCH_2CH_2OS$—), 4.34(t, 1H, ArCH), 7.33(m, 5H, ArH)

ESI-TOF (+): $[M+Na]^+$382.2

(5) Synthesis of [2-(2-iodo-ethoxy)-2-phenyl-ethyl]-carbamic acid tert-butyl ester (Compound 6)

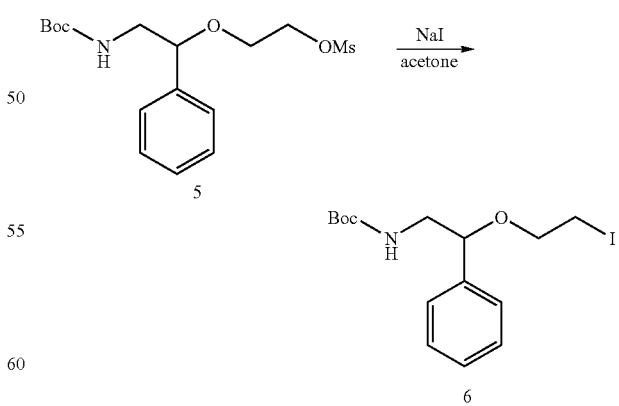

To a 50 ml eggplant type flask, 100 mg (0.28 mmol) of Compound 5 was added and the atmosphere was changed to nitrogen. Then 10 ml of acetone and 1.0 g (6.67 mmol) of NaI were added, and the mixture was heated to reflux for 2 hours. After removing NaI by filtration, the solvent was evaporated under reduced pressure. The residue was purified by column chromatography (SiO₂, n-hexane:ethyl acetate=1:1 v/v) to obtain a yellow oily compound (104 mg, Yield: 93.99%).

$^1$H-NMR (270 MHz, CDCl₃, TMS, r.t., δ/ppm) 1.45(s, 9H, t-Bu) 3.22(t, 2H, I—CH₂), 3.49(d, 2H, NH—CH₂), 3.67(t, 2H, —OCH₂), 4.43(t, 1H, ArCH), 7.34(m, 5H, ArH) ESI-TOF (+): [M+Na]⁺413.9

(6) Synthesis of [2-(2-tert-butoxycarbonylamino-1-phenyl-ethoxy)-ethyl]-triethyl-ammonium iodide (Compound 7)

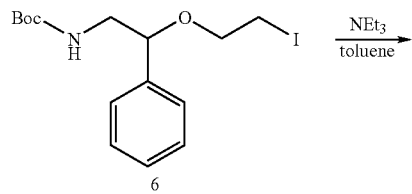

To a 50 ml eggplant type flask, 350 mg (0.90 mmol) of Compound 6, 8.75 ml of toluene and 1.75 ml (17.33 mmol) of TEA were added, and the reaction was carried out at 80° C. for 24 hours. After evaporating the solvent under reduced pressure, the residue-was purified by large thin layer chromatography (SiO₂, chloroform:methanol 7:1 v/v) to obtain a reddish yellow solid product (383 mg, Yield: 66.70%).

$^1$H-NMR (300 MHz, CDCl₃, TMS, r.t., δ/ppmr) 1.42(t, 9H, CH₂—CH₃), 1.48(s, 9H, t-Bu), 3.53(q, 6H, NR₃—CH₂), 3.70(t, 2H, —OCH₂CH₂N—), 3.72(d, 2H, NH—CH₂), 3.95(t, 2H, —OCH₂CH₂N—), 4.63(t, 1H, ArCH), 7.35(m, 5H, ArH) ESI-TOF (+): [M]⁺=365.2

(7) Synthesis of Compound 8

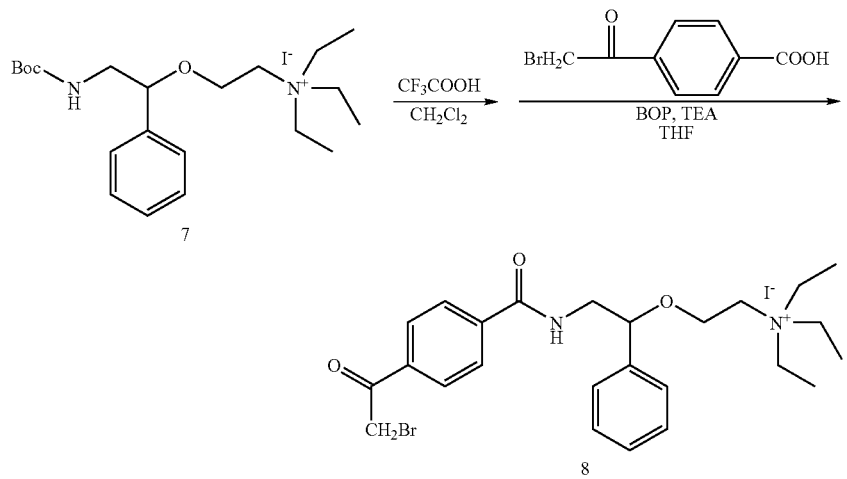

To a 30 ml eggplant type flask, 0.50 g (1.02 mmol) of Compound 7, 0.50 ml of TFA (trifluoroacetic acid) and 10.0 ml of methylene chloride were added, and the mixture was stirred at room temperature for 30 minutes. The solvent was evaporated under reduced pressure and the resultant was dried under reduced pressure using a pump. After changing the atmosphere to nitrogen, 20.0 ml of THF, 0.10 g (1.02 mmol) of TEA, 0.10 g (1.02 mmol) of BOP and 0.25 g (1.02 mmol) of 4-bromomethylacetylbenzoic acid were added, and the mixture was stirred at room temperature for 24 hours. After evaporating the solvent under reduced pressure, the residue was purified by column chromatography to obtain the desired compound.

(8) Synthesis of Compound 9

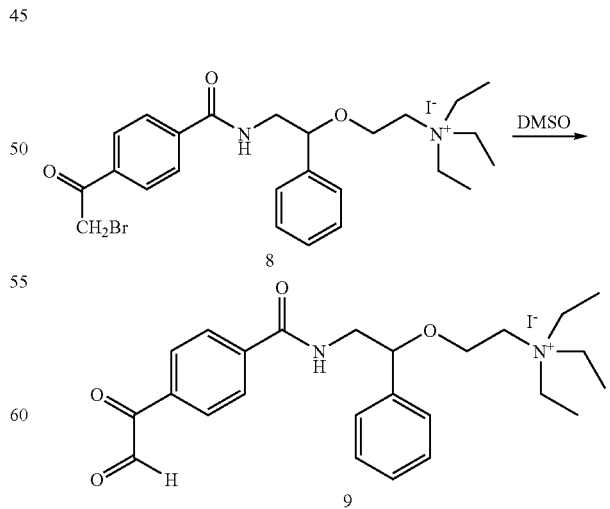

To a 20 ml eggplant type flask, 0.25 g (0.41 mmol) of Compound 8 and 5.0 ml of DMSO were added, and the mixture was stirred at room temperature for 2 hours. After evaporating the solvent under reduced pressure, the residue was purified by column chromatography to obtain the desired compound.

EXAMPLE 6

Synthesis of Probe (No. 6)

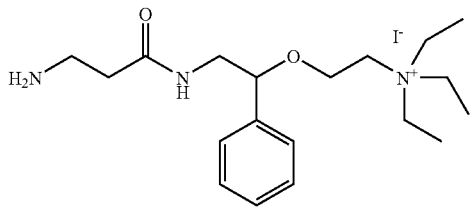

In accordance with the scheme below, the above-described compound having a quaternary amine as $R^1$ and —CH$_2$CH$_2$NH$_2$ as $R^2$ was synthesized.

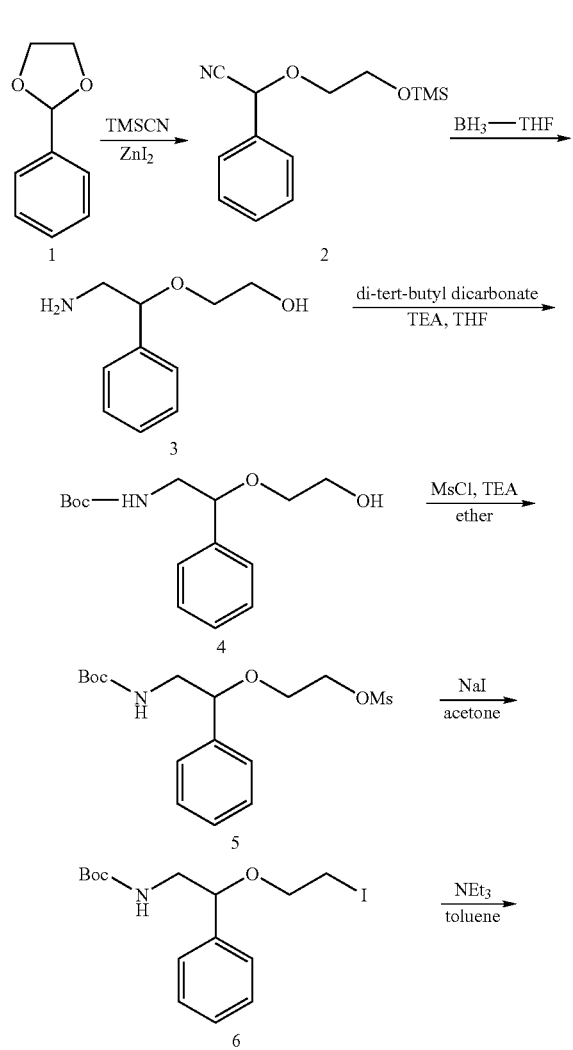

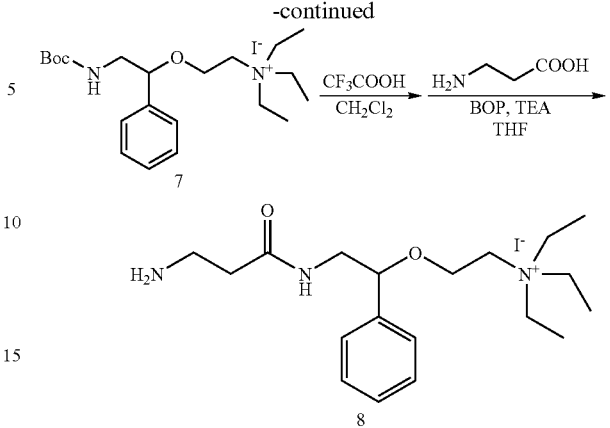

(1) Synthesis of phenyl-(2-trimethylsilanyloxy-ethoxy)-acetonitrile (Compound 2)

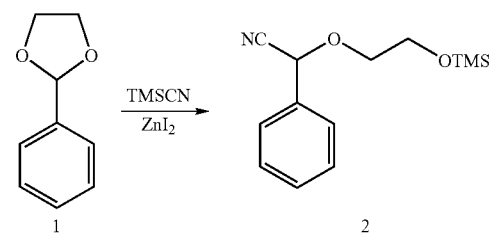

To a 30 ml eggplant type flask, 3.0 g (19.9 mmol) of 2-phenyl-1,3-pentadione (Compound 1) was added and the flask was dipped in an ice bath. To the flask, 2.1 ml (21.43 mmol) of TMSCN and 0.3 g (0.94 mmol) of ZnI$_2$ were added, and the mixture was stirred at room temperature for 2 hours. Diethyl ether was added to the reaction solution and the mixture was washed with water, followed by drying using MgSO$_4$. The solvent was evaporated under reduced pressure to obtain a yellow oily product (4.17 g, yield: 83.2%).

$^1$H-NMR (270 MHz, CDCl$_3$, TMS, r.t., δ/ppm) 0.15 (s, 9H, SiCH$_3$), 3.80 (t, 2H, —OCH$_2$CH$_2$OSi—), 4.11 (t, 2H, —OCH$_2$CH$_2$OSi—), 5.39 (s, 1H, ArCH), 7.45 (m, 5H, ArH)ESI-TOF(+): [M+Na]$^+$=272.0

(2) Synthesis of 2-(2-amino-1-phenyl-ethoxy)-ethanol (Compound 3)

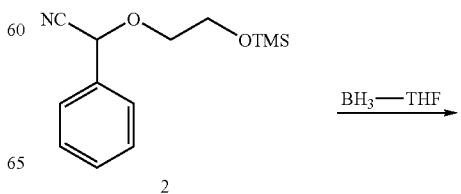

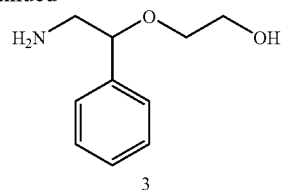

To a 100 ml three-necked flask, 1.0 g (4.01 mmol) of Compound 2 was added and the atmosphere was changed to nitrogen after degassing. The flask was dipped in an ice bath and 30 ml of 1M $BH_3$ solution in THF was slowly added. The resulting mixture was stirred for 30 minutes while cooling the mixture in ice and then at room temperature for 4 hours. After completion of the reaction, the reaction vessel was dipped in an ice bath and aqueous 1N HCl solution was added, thereby making the mixture acidic. After evaporating the solvent under reduced pressure, 20 ml of water was added and aqueous NaOH solution was added to adjust the pH to 10. The mixture was extracted with ethyl acetate and the organic phase was washed with water, followed by drying over anhydrous sodium sulfate to obtain a colorless oily compound (650 mg, Yield: 89.5%).

$^1$H-NMR (300 MHz, $CDCl_3$, TMS, r.t., δ/ppm) 2.95(d, 2H, $NH_2$—$CH_2$), 3.65(t, 2H, —$OCH_2CH_2OH$), 3.75(t, 2H, —$OCH_2CH_2OH$), 4.46(t, 1H, ArCH), 7.32(m, 5H, ArH) ESI-TOF (+): [M+H]$^+$=182.0

(3) Synthesis of [2-(2-hydroxy-ethoxy)-2-phenyl-ethyl]-carbamic acid tert-butyl ester

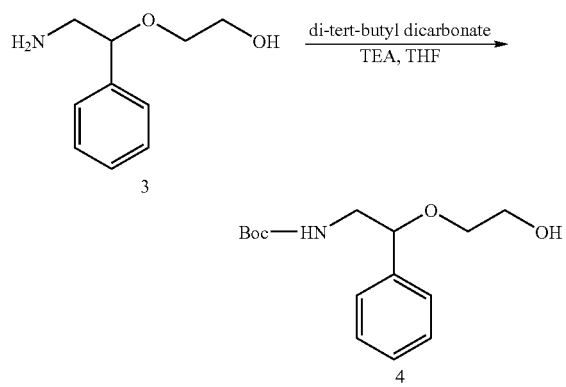

To a 100 ml two-necked flask, 1.40 g (7.70 mmol) of Compound 3 was added and the atmosphere was changed to nitrogen. While cooling the flask in a ice bath, 55 ml of anhydrous THF, 0.78 g (7.69 mmol) of TEA and 1.68 g (7.70 mmol) of di-tert-butyl-dicarbonate were added, and the mixture was stirred at room temperature for 2 hours. The solvent was evaporated under reduced pressure and the residue was purified by column chromatography ($SiO_2$, chloroform) to obtain a yellow oily compound (1.30 g, Yield: 59.9%).

$^1$H-NMR (300 MHz, $CDCl_3$, TMS, r.t., δ/ppm) 1.48(s, 9H, t-Bu), 3.24(d, 2H, NH—$CH_3$), 3.49(t, 2H, —$OCH_2CH_2OH$), 3.73(t, 2H, —$OCH_2CH_2OH$) 4.42(t, 1H, ArCH), 7.33(m, 5H, ArH) ESI-TOF (+): [M+Na]$^+$=304.0

(4) Synthesis of methanesulfonic acid-2-(2-tert-butoxycarbonylamino-1-phenyl-ethoxy) ethyl ester (Compound 5)

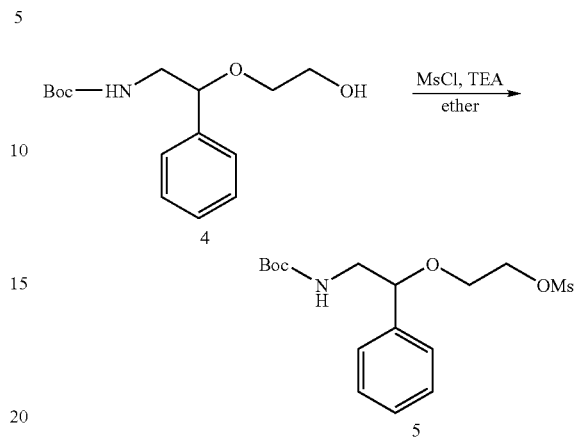

To a 50 ml eggplant type flask, 100 mg (0.28 mmol) of Compound 5 was added and the atmosphere was changed to nitrogen. Then 10 ml of acetone and 1.0 g (6.67 mmol) of NaI were added, and the mixture was heated to reflux for 2 hours. After removing NaI by filtration, the solvent was evaporated under reduced pressure. The residue was purified by column chromatography ($SiO_2$, n-hexane:ethyl acetate=1:1 v/v) to obtain a yellow oily compound (104 mg, Yield: 93.99%).

$^1$H-NMR (270 MHz, $CDCl_3$, TMS, r.t., δ/ppm) 1.45(s, 9H, t-Bu), 3.22(t, 2H, I—$CH_2$), 3.49(d, 2H, NH—$CH_2$), 3.67(t, 2H, —$OCH_2$), 4.43(t, 1H, ArCH), 7.34(m, 5H, ArH) ESI-TOF (+): [M+Na]$^+$=413.9

(5) Synthesis of [2-(2-iodo-ethoxy)-2-phenyl-ethyl]-carbamic acid tert-butyl ester (Compound 6)

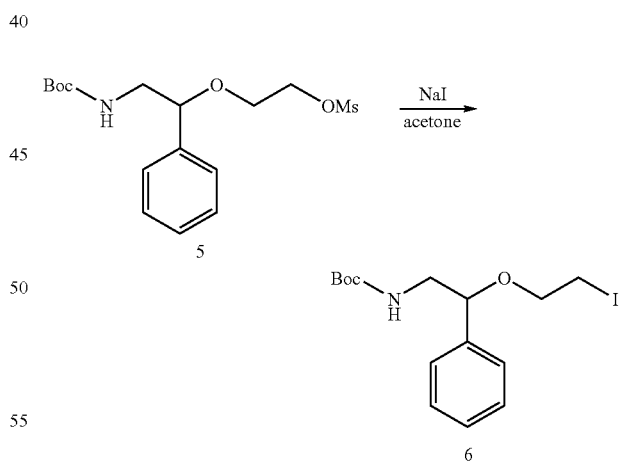

To a 50 ml eggplant type flask, 100 mg (0.28 mmol) of Compound 5 was added and the atmosphere was changed to nitrogen. Then 10 ml of acetone and 1.0 g (6.67 mmol) of NaI were added, and the mixture was heated to reflux for 2 hours. After removing NaI by filtration, the solvent was evaporated under reduced pressure. The residue was purified by column chromatography ($SiO_2$, n-hexane:ethyl acetate=1:1 v/v) to obtain a yellow oily compound (104 mg, Yield: 93.99%).

$^1$H-NMR (270 MHz, CDCl$_3$, TMS, r.t., δ/ppm) 1.45(s, 9H, t-Bu), 3.22(t, 2H, I—CH$_2$), 3.49(d, 2H, NH—CH$_2$), 3.67(t, 2H, —OCH$_2$), 4.43(t, 1H, ArCH), 7.34(m, 5H, ArH) ESI-TOF (+): [M+Na]$^+$413.9

(6) Synthesis of [2-(2-tert-butoxycarbonylamino-1-phenyl-ethoxy)-ethyl]-triethyl-ammonium iodide (Compound 7)

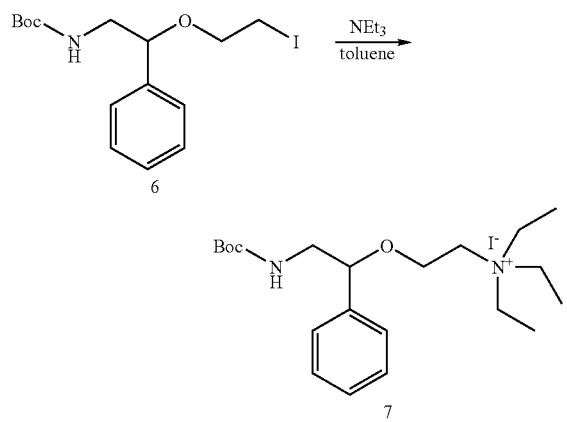

To a 50 ml eggplant type flask, 350 mg (0.90 mmol) of Compound 68.75 ml of toluene and 1.75 ml (17:33 mmol) of TEA were added, and the reaction was carried out at 80° C. for 24 hours. After evaporating the solvent under reduced pressure, the residue was purified by large thin layer chromatography (SiO$_2$, chloroform:methanol=7:1 v/v) to obtain a reddish yellow solid product (383 mg, Yield: 66.70%).

$^1$H-NMR (300 MHz, CDCl$_3$, TMS, r.t., δ/ppm) 1.42(t, 9H, CH$_2$—CH$_3$), 1:48(s, 9H, t-Bu), 3.53(q, 6H, NR$_3$—CH$_2$), 3.70(t, 2H, —OCH$_2$CH$_2$N—), 3.72(d, 2H, NH—CH$_2$), 3.95 (t, 2H, —OCH$_2$CH$_2$N—), 4.63(t, 1H, ArCH), 7.35(m, 5H, ArH) ESI-TOF (+): [M]$^+$=365.2

(7) Synthesis of Compound 8

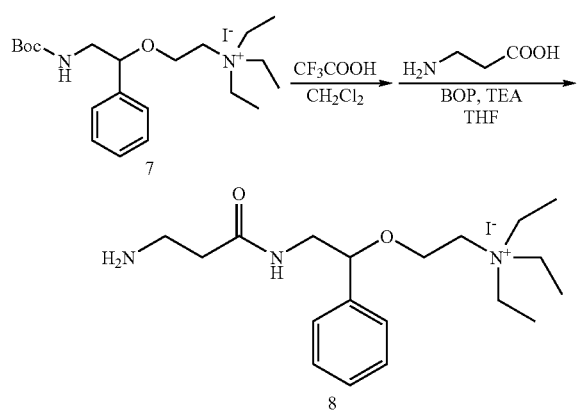

To a 30 ml eggplant type flask, 0.50 g (1.02 mmol) of Compound 7, 0.50 ml of TFA and 10.0 ml of methylene chloride were added, and the mixture was stirred at room temperature for 30 minutes. The solvent was evaporated under-reduced pressure and the resultant was dried under reduced pressure using a pump. After changing the atmosphere to nitrogen, 20.0 ml of THF, 0.10 g (1.02 mmol) of TEA, 0.10 g (1.02 mmol) of BOP and 0.10 g (1.02 mmol) of O-alanine were added, and the mixture was stirred at room temperature for 24 hours. After evaporating the solvent under reduced pressure, the residue was purified by column chromatography to obtain the desired compound.

EXAMPLE 7

Synthesis of Probe (No. 7)

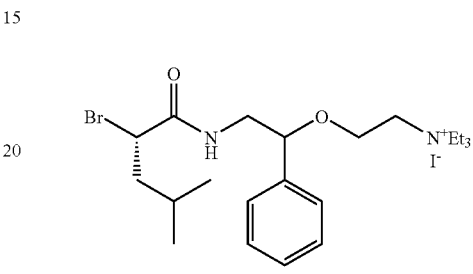

In accordance with the scheme below, the above-described compound having a quaternary amine as R$^1$ and

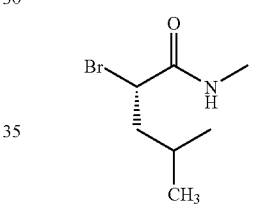

as R$^2$ was synthesized.

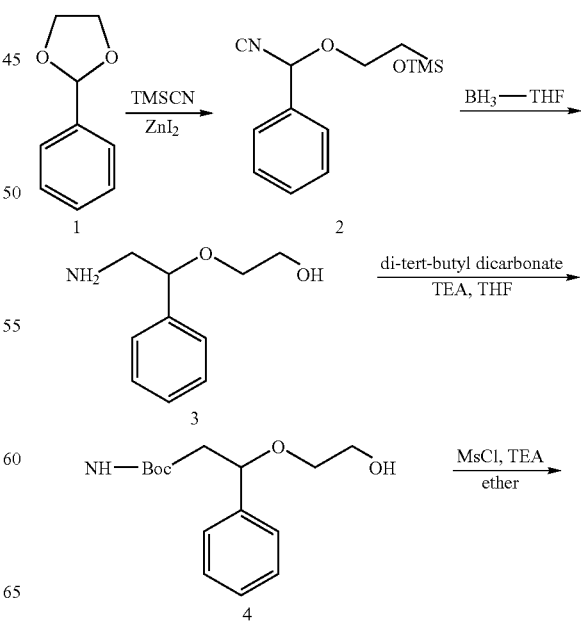

—OCH$_2$CH$_2$OSi—), 5.39(s, 1H, ArCH), 7.45(m, 5H, ArH) ESI-TOF(+): [M+Na]$^+$=272.0

(2) Synthesis of 2-(2-amino-1-phenyl-ethoxy)-ethanol (Compound 3)

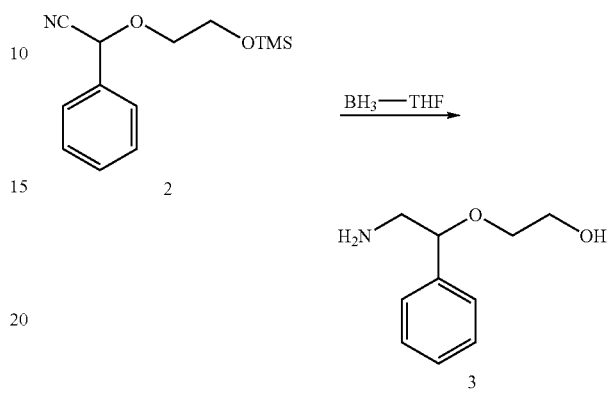

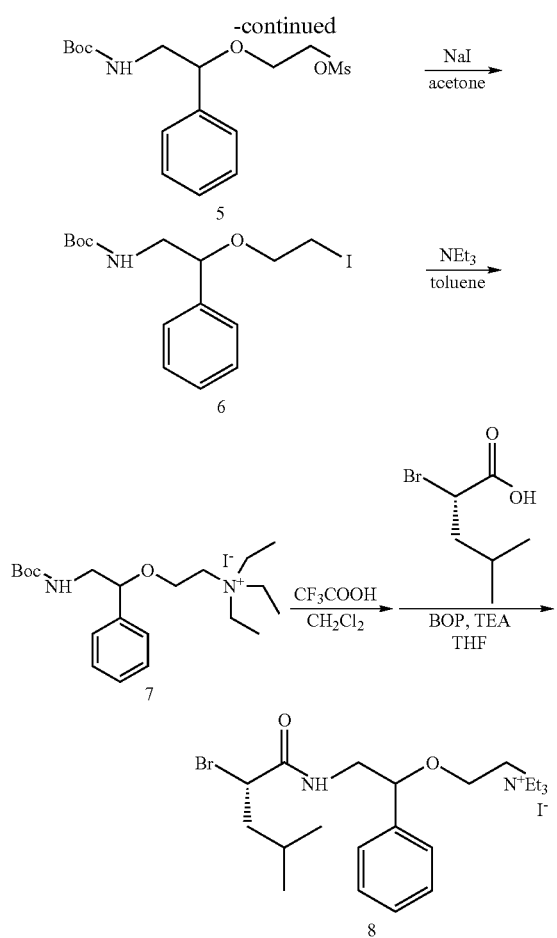

To a 100 ml three-necked flask, 1.0 g (4.01 mmol) of Compound 2 was added and the atmosphere was changed to nitrogen after degassing. The flask was dipped in an ice bath and 30 ml of 1M BH$_3$ solution in THF was slowly added. The resulting mixture was stirred for 30 minutes while cooling the mixture in ice and then at room temperature for 4 hours. After completion of the reaction, the reaction vessel was dipped in an ice bath and aqueous 1N HCl solution was added, thereby making the mixture acidic. After evaporating the solvent under reduced pressure, 20 ml of water was added and aqueous NaOH solution was added to adjust the pH to 10. The mixture was extracted with ethyl acetate and the organic phase was washed with water, followed by drying over anhydrous sodium sulfate to obtain a colorless oily compound (650 mg, Yield: 89.5%).

$^1$H-NMR (300 MHz, CDCl$_3$, TMS, r.t., δ/ppm) 2.95(d, 2H, NH$_2$—CH$_2$), 3.65(t, 2H, —OCH$_2$CH$_2$OH), 3.75(t, 2H, —OCH$_2$CH$_2$OH), 4.46(t, 1H, ARCH), 7.32(m, 5H, ArH) ESI-TOF (+): [M+H]$^+$182.0

(3) Synthesis of [2-(2-hydroxy-ethoxy)-2-phenyl-ethyl]-carbamic acid tert-butyl ester

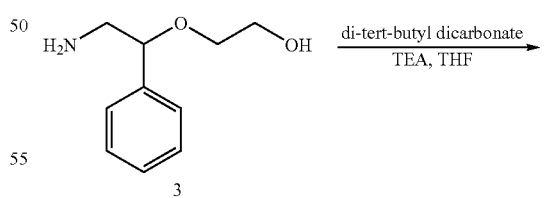

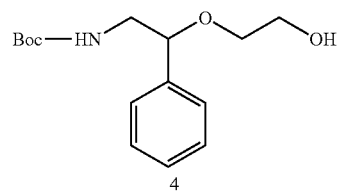

(1) Synthesis of phenyl-(2-trimethylsilanyloxy-ethoxy)-acetonitrile (Compound 2)

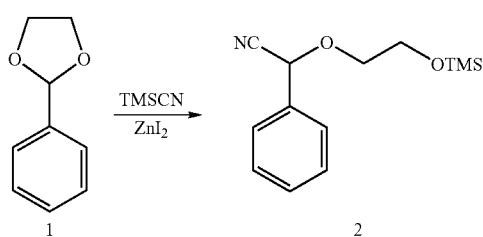

To a 30 ml eggplant type flask, 3.0 g (19.9 mmol) of 2-phenyl-1,3-pentadione (Compound 1) was added and the flask was dipped in an ice bath. To the flask, 2.1 ml (21.43 mmol) of TMSCN and 0.3 g (0.94 mmol) of ZnI$_2$ were added, and the mixture was stirred at room temperature for 2 hours. Diethyl ether was added to the reaction solution and the mixture was washed with water, followed by drying using MgSO$_4$. The solvent was evaporated under reduced pressure to obtain a yellow oily product (4.17 g, yield: 83.2%).

$^1$H-NMR (270 MHz, CDCl$_3$, TMS, r.t., δ/ppm) 0.15(s, 9H, SiCH$_3$), 3.80(t, 2H, —OCH$_2$CH$_2$OSi—), 4.11(t, 2H, To a 100 ml two-necked flask, 1.40 g (7.70 mmol) of Compound 3 was added and the atmosphere was changed to nitrogen. While cooling the flask in an ice bath, 55 ml of anhydrous THF, 0.78 g (7.69 mmol) of TEA and 1.68 g (7.70 mmol) of di-tert-butyl-dicarbonate were added, and the mixture was stirred at room temperature for 2 hours. The solvent was evaporated under reduced pressure and the residue was purified by column chromatography (SiO$_2$, chloroform) to obtain a yellow oily compound (1.30 g, Yield: 59.9%).

$^1$H-NMR (300 MHz, CDCl$_3$, TMS, r.t., δ/ppm) 1.48(s, 9H, t-Bu), 3.24(d, 2H, NH—CH$_3$), 3.49(t, 2H, —OCH$_2$CH$_2$QH), 3.73(t, 2H, —OCH$_2$CH$_2$OH), 4.42(t, 1H, ArCH), 7.33(m, 5H, ArH) ESI-TOF (+): [M+Na]$^+$=304.0

(4) Synthesis of methanesulfonic acid 2-(2-tert-butoxycarbonylamino-1-phenyl-ethoxy) ethyl ester (Compound 5)

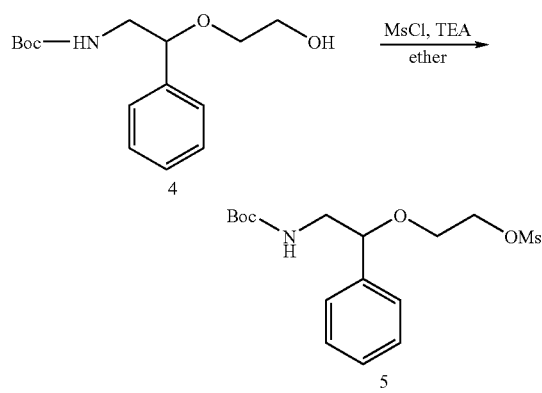

To a 50 ml eggplant type flask, 500 mg (1.78 mmol) of Compound 4 was added and the atmosphere was changed to nitrogen. Then 16 ml of anhydrous THF and 0.5 ml (4.55 mmol) of TEA were added and the flask was dipped in an ice bath. To the mixture, 440 mg (3.84 mmol) of MsCl was added and the resulting mixture was stirred at room temperature for 1 hour. After evaporating the solvent under reduced pressure, chloroform was added and the generated precipitates were removed by filtration, followed by concentrating the filtrate under reduced pressure. The resulting product was purified by column chromatography (SiO$_2$, ethyl acetate: n-hexane=2:1 v/v) to obtain a yellow oily product (491 mg, Yield: 77.0%).

$^1$H-NMR (300 MHz, CDCl$_3$, TMS, r.t., δ/ppm) 1.44(s, 9H, t-Bu), 3.24(d, 2H, NH—CH$_2$), 3.44(t, 2H, —OCH$_2$CH$_2$OS—), 3.62(t, 2H, —OCH$_2$CH$_2$OS—), 4.34(t, 1H, ArCH), 7.33(m, 5H, ArH) ESI-TOF (+): [M+Na]$^+$382.2

(5) Synthesis of [2-(2-iodo-ethoxy)-2-phenyl-ethyl]-carbamic acid tert-butyl ester (Compounds 6)

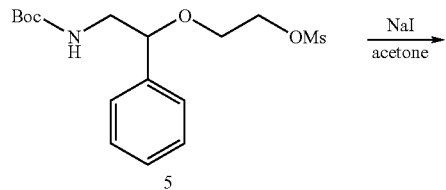

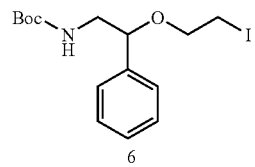

To a 50 ml eggplant type flask, 100 mg (0.28 mmol) of Compound 5 was added and the atmosphere was changed to nitrogen. Then 10 ml of acetone and 1.0 g (6.67 mmol) of NaI were added, and the mixture was heated to reflux for 2 hours. After removing NaI by filtration, the solvent was evaporated under reduced pressure. The residue was purified by column chromatography (SiO$_2$, n-hexane:ethyl acetate=1:1 v/v) to obtain a yellow oily compound (104 mg, Yield: 93.99%).

$^1$H-NMR (270 MHz, CDCl$_3$, TMS, r.t., δ/ppm) 1.45 (s, 9H, t-Bu), 3.22 (t, 2H, I—CH$_2$), 3.49 (d, 2H, NH—CH$_2$), 3.67(t, 2H, —OCH$_2$), 4.43(t, 1H, ArCH), 7.34(m, 5H, ArH) ESI-TOF (+): [M+Na]$^+$=413.9

(6) Synthesis of [2-(2-tert-butoxycarbonylamino-1-phenyl-ethoxy)-ethyl]-triethyl-ammonium iodide (Compound 7)

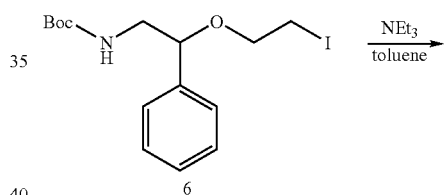

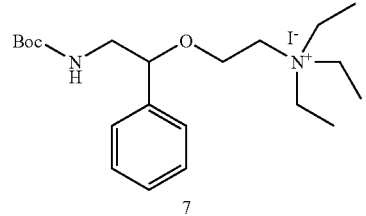

To a 50 ml eggplant type flask, 350 mg (0.90 mmol) of Compound 6, 8.75 ml of toluene and 1.75 ml (17.33 mmol) of TEA were added, and the reaction was carried out at 80° C. for 24 hours. After evaporating the solvent under reduced pressure, the residue was purified by large thin layer chromatography (SiO$_2$, chloroform:methanol=7:1 v/v) to obtain a reddish yellow solid product (383 mg, Yield: 66.70%).

$^1$H-NMR (300 MHz, CDCl$_3$, TMS, r.t., δ/ppm) 1.42(t, 9H, CH$_2$—CH$_3$), 1.48(s, 9H, t-Bu), 3.53(q, 6H, NR$_3$—CH$_2$), 3.70(t, 2H, —OCH$_2$CH$_2$N—), 3.72(d, 2H, NH—CH$_2$), 3.95 (t, 2H, —OCH$_2$CH$_2$N—), 4.63(t, 1H, ArCH), 7.35(m, 5H, ArH) ESI-TOF (+): [M]$^+$=365.2

(7) Synthesis of Compound 8

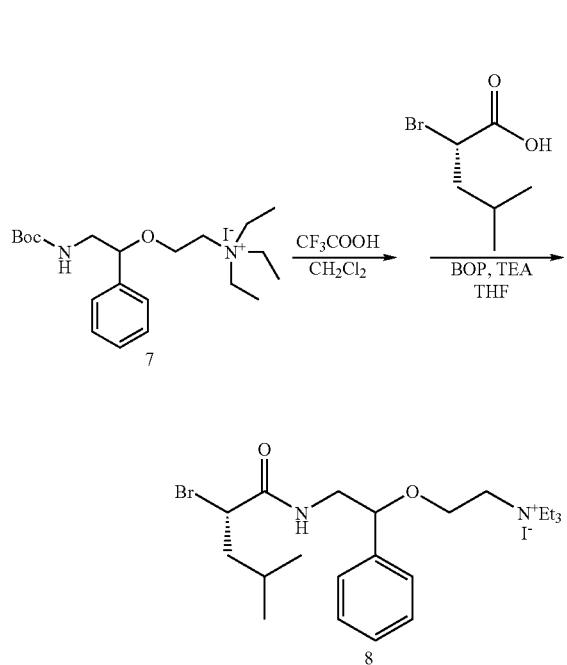

To a 30 ml eggplant type flask, 0.50 g (1.02 mmol) of Compound 7, 0.50 ml of TFA and 10.0 ml of methylene chloride were added, and the mixture was stirred at room temperature for 30 minutes. The solvent was evaporated under reduced pressure and the resultant was dried under reduced pressure using a pump. After changing the atmosphere to nitrogen, 20.0 ml of THF, 0.10 g (1.02 mmol) of TEA, 0.10 g (1.02 mmol) of BOP and 0.20 g (1.02 mmol) of 2-bromo-4-methylpentanoic acid were added, and the mixture was stirred at room temperature for 24 hours. After evaporating the solvent under reduced pressure, the residue was purified by column chromatography to obtain the desired compound.

EXAMPLE 8

Synthesis of Probe (No. 8)

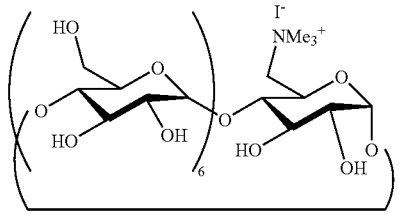

In accordance with the scheme below, the above-described compound having a quaternary amine as $R^1$ and cyclodextrin (the number of glucopyranose: 7) as $R^2$ was synthesized.

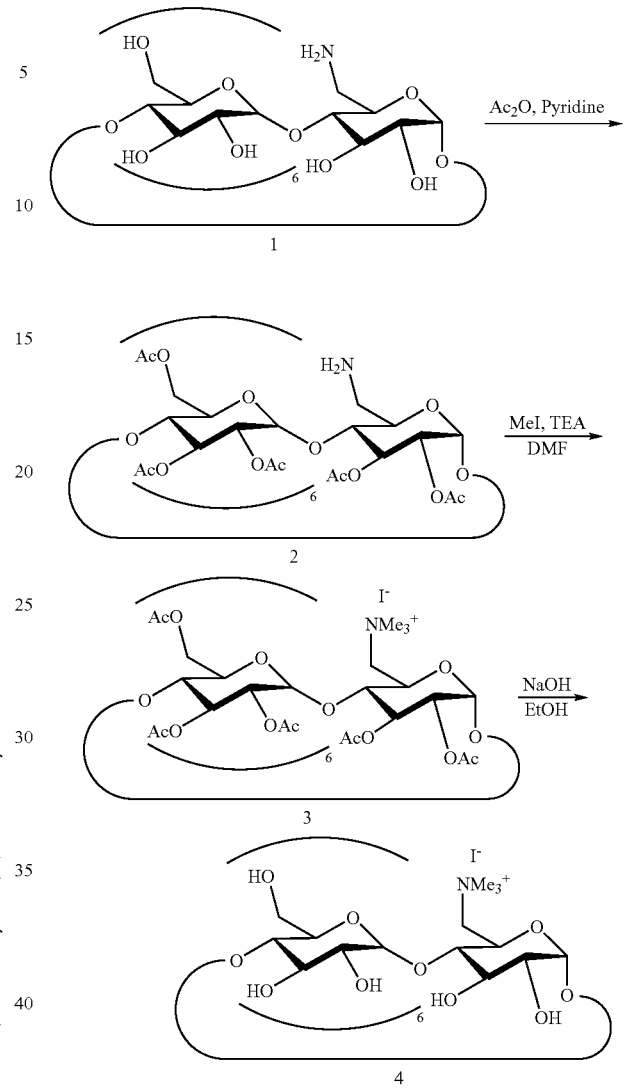

(1) Synthesis of Compound 2

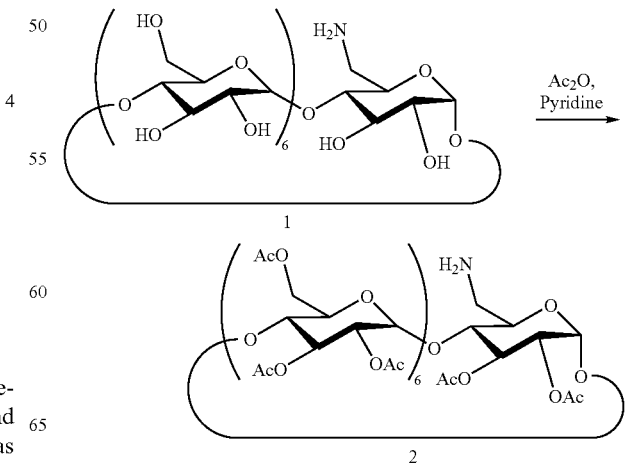

To a 100 ml eggplant type flask, 2.0 g (1.59 mmol) of mono-6-deoxy-6-amino-β-cyclodextrin (1), 20.0 ml of acetic anhydride and 10.0 ml of pyridine were added, and the mixture was stirred at room temperature for 24 hours. The reaction solution was poured into cold water and the resulting mixture was extracted with ether. The resulting mixture was washed with saturated saline and dried over anhydrous sodium sulfate, followed by evaporation of the solvent under reduced pressure to obtain the desired compound.

(2) Synthesis of Compound 3

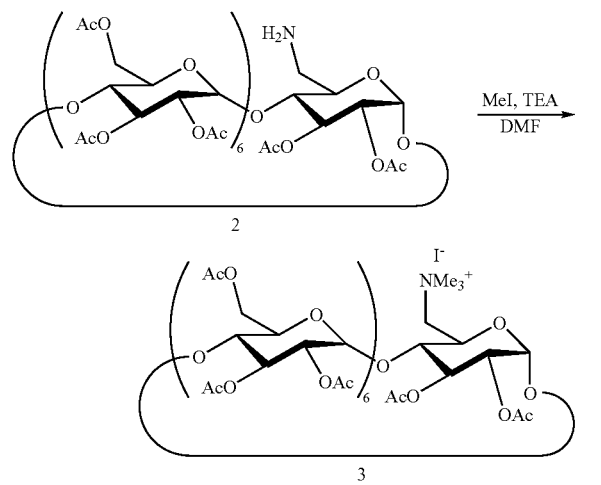

To a 100 ml three-necked flask, 1.0 g (0.37 mmol) of Compound 2, 0.26 g (1.85 mmol) of methyl iodide, 0.05 g (0.40 mmol) of trimethylamine and 20.0 ml of anhydrous DMF were added, and the mixture was stirred at room temperature for 24 hours under nitrogen gas flow. After evaporating the solvent under reduced pressure, reprecipitation operation was carried out to obtain the desired compound.

(3) Synthesis of Compound 4

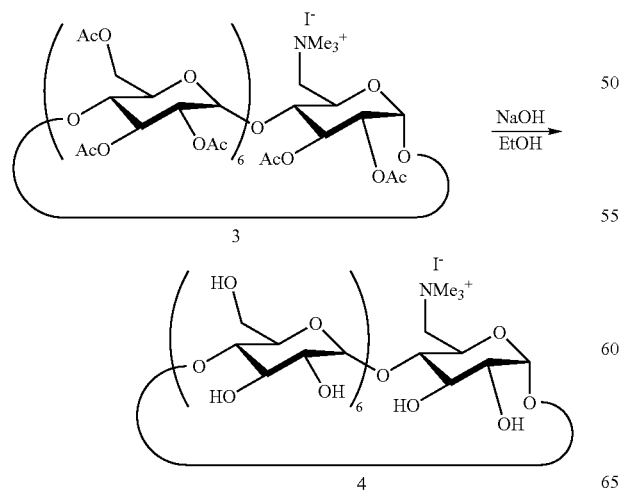

To a 50 ml eggplant type flask, 1.0 g (0.35 mmol) of Compound 3 5.0 ml of 1.0M aqueous NaOH solution and 20.0 ml of ethanol were added, and the mixture was heated to reflux for 5 hours. After evaporating most of the solvent under reduced pressure, 20 ml of water was added and the mixture was acidified with 1N HCl. After evaporating the solvent under reduced pressure, reprecipitation operation was carried out to obtain the desired compound.

EXAMPLE 9

Synthesis of Probe (No. 9)

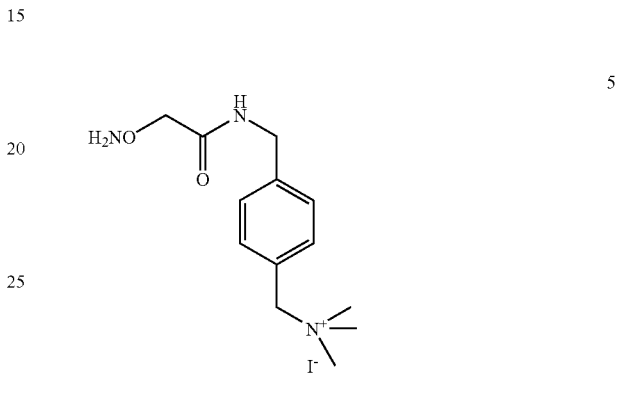

In accordance with the scheme below, the above-described compound having a quaternary amine as $R^1$ and —$ONH_2$ as $R^2$ was synthesized.

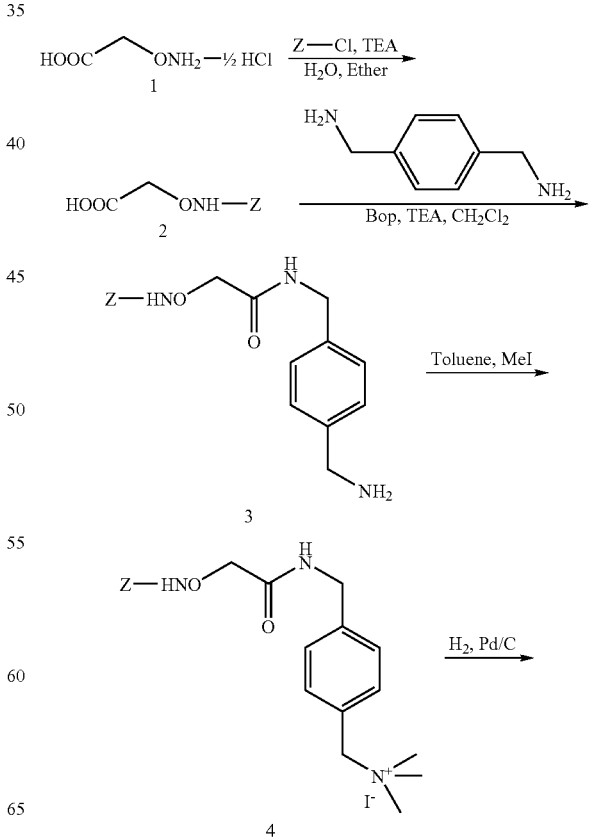

-continued

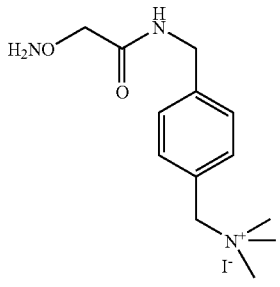
5

(1) Synthesis of Compound 2

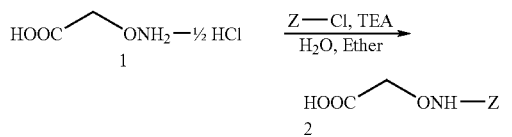

To a 100 ml eggplant type flask, 3.0 g (27.5 mmol) of Compound 1, 30.0 ml of water and 3.46 g (34.3 mmol) of triethylamine were added, and the flask was dipped in an ice bath. In 10.0 ml of diethyl ether, 4.8 g (27.5 mmol) of Z chloride was dissolved and the obtained solution was added to the mixture using a dropping funnel. The resulting mixture was stirred for 30 minutes in an ice bath and then for 7 hours at room temperature. After extraction of the mixture with ethyl acetate, the organic layer was washed with saturated saline. The resultant was dried over anhydrous sodium sulfate, and the residue was purified by column chromatography (SiO$_2$, CHCl$_3$:ethyl acetate=2:3 v/v) to obtain the desired compound.

(2) Synthesis of Compound 3

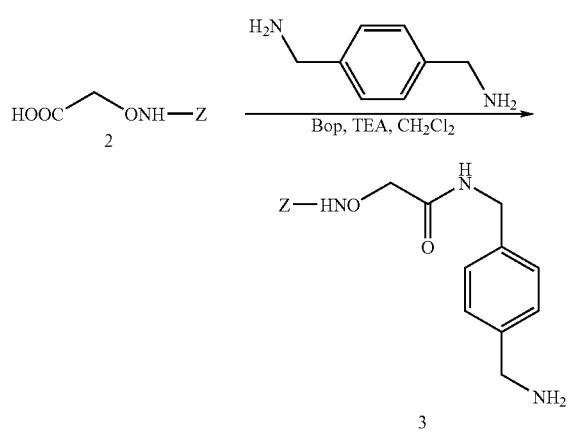

To a 100 ml three-necked flask, 2.0 g (10.3 mmol of Compound 2, 50.0 ml of anhydrous methylene chloride and 1.1 g(11.0 mmol) of triethylamine were added, and the flask was dipped in an ice bath. To the mixture, 1.4 g (11.0 mmol) of p-xylylenediamine and 4.8 g (11.0 mmol) of BOP reagent were added, and the resulting mixture was stirred in an iced bath for 30 minutes and then at room temperature for 12 hours. After stopping the reaction by adding water, the mixture was washed with saturated saline and dried over anhydrous sodium sulfate. After evaporating the solvent under reduced pressure, the residue was purified by column chromatography (SiO$_2$, CHCl$_3$:ethyl acetate=1:1 v/v) to obtain the desired compound.

(3) Synthesis of Compound 4

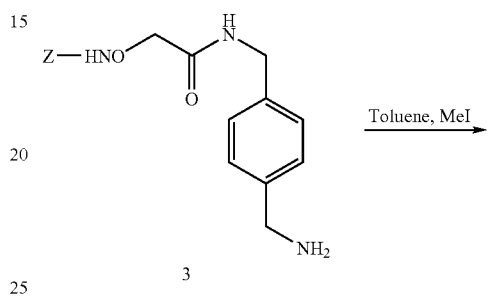

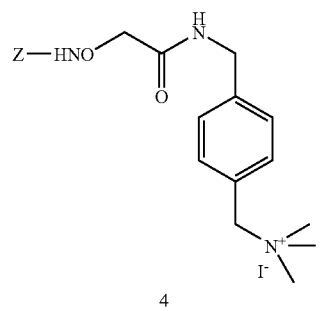

To a 100 ml eggplant type flask, 2.0 g (6.0 mmol) of Compound 3, 50.0 ml of toluene and 8.5 g (60.0 mmol) of methyl iodide were added, and the mixture was heated at 80° C. under stirring. The generated precipitates were recovered and washed with toluene to obtain the desired compound.

(4) Synthesis of Compound 5

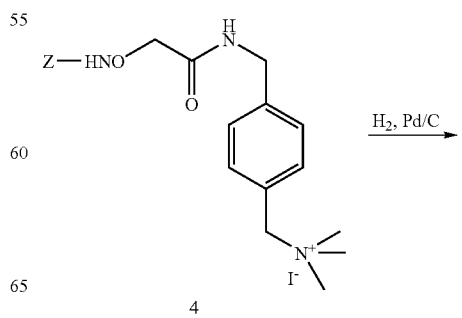

-continued

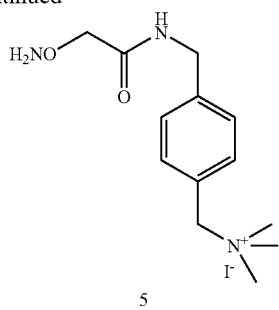

To a 100 ml eggplant type flask, 2.0 g (5.0 mmol) of Compound 4 and ethanol were added, and the atmosphere was changed to nitrogen, and then to hydrogen. To the mixture, 0.1 g of palladium-carbon was added and the mixture was stirred at room temperature for 5 hours. After removing the palladium-carbon by filtration, the solvent was evaporated under reduced pressure to obtain the desired compound.

EXAMPLE 10

Synthesis of Probe (No. 10)

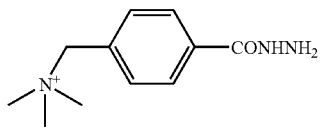

In accordance with the scheme below the above-described compound having a quaternary amine as $R^1$ and —NHNH$_2$ as $R^2$ was synthesized.

(1) Synthesis of Compound 2

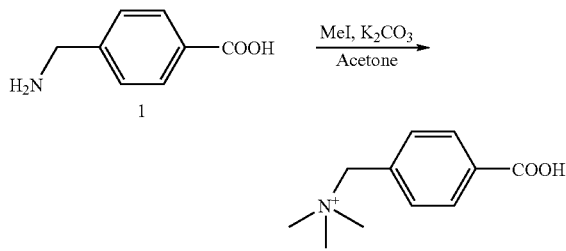

To a 100 ml eggplant type flask, 3.0 g (19.8 mmol) of Compound 1, 50.0 ml of acetone, 14.1 g (100.0 mmol) of methyl iodide and 6.9 g (50.0 mmol) of potassium carbonate were added, and the mixture was heated to reflux for 24 hours under nitrogen gas flow. After removing potassium carbonate by filtration, the solvent was evaporated under reduced pressure. Chloroform was added to the reaction mixture and the generated precipitates were recovered, followed by washing the precipitates with chloroform to obtain the desired compound.

(2) Synthesis of Compound 3

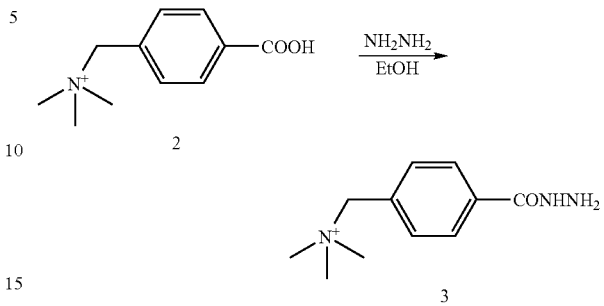

To a 100 ml eggplant type flask, 2.0 g (6.25 mmol) of Compound 2, 30.0 ml of ethanol and 0.22 g (7.0 mmol) of hydrazine were added, and the mixture was stirred at room temperature for 5 hours. The solvent was evaporated under reduced pressure to obtain the desired product.

EXAMPLE 11

Electrospray Ionization Mass Spectrometry (1) Binding between Sample Compound and Probe As shown in the reaction equation below, the probe (Compound 1) synthesized in Example 1 and a sample compound (Compound 2) were bound. This reaction was carried out by adding 10.0 mM of Compound 1 and a solution of Compound 2 in acetonitrile (or in THF) to a test tube, mixing the reactants, and by stirring the mixture at room temperature for 30 minutes.

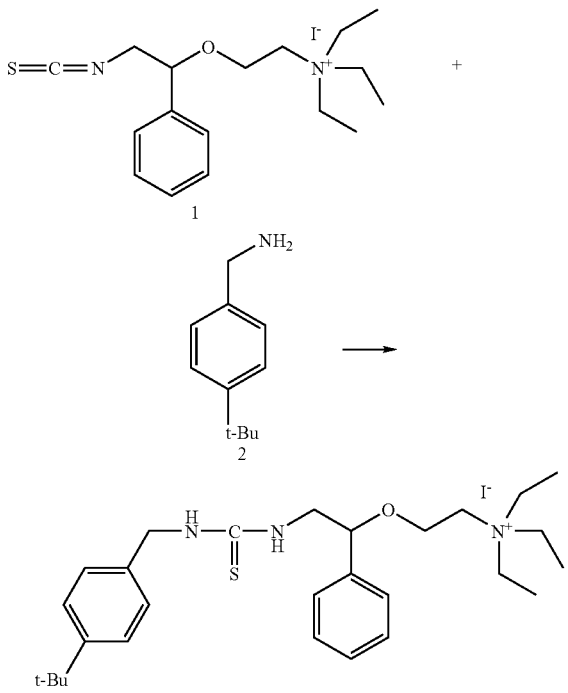

(2) Electrospray Ionization Mass Spectrometry

Figure 3:
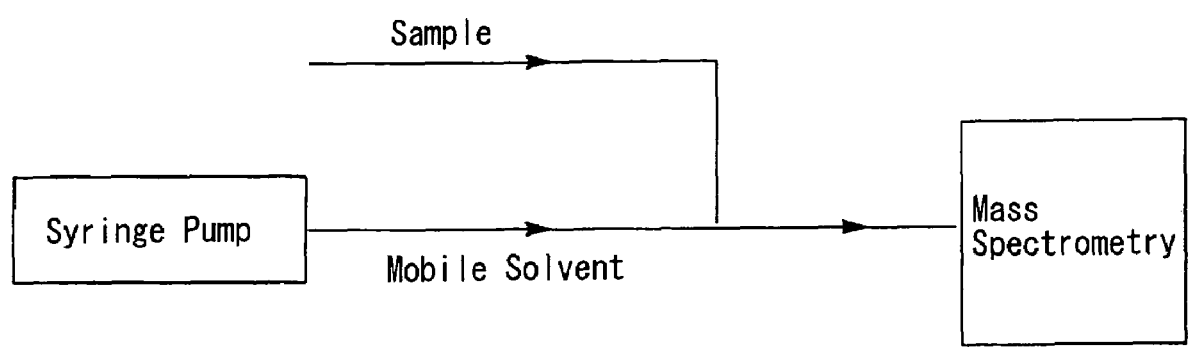
FIG. 3 schematically shows the constitution of mass spectrometer used in the mass spectrometry carried out in Example 11.

After diluting the reaction product obtained in (1) to 1.0 μM, measurement was carried out using ESI-TOF mass spectrometer (Mariner) produced by Applied Biosystems. The constitution of the mass spectrometer is shown in FIG. 3; From a syringe pump, continuously moving solvent (MeOH, water or the like) was streamed at a flow rate of 10.0 μL/min. The sample solution was introduced from an injector using a microsyringe. The sample solution moves to the mass spectrometer along the flow of the mobile solvent.

The set conditions of the mass spectrometer were as follows:
Spray tip potential: 3450 V
Nozzle Potential: 184 V
Quad RF voltage: 1000 V
Flow rate of Nebulizer gas ($N_2$): 0.25 L/min.
Flow rate of Auxiliary gas ($N_2$): 1.0 L/min.
Temperature of the counter stream: 160° C.

The results of the measurement are shown in FIG. 1. For comparison, the probe alone was subjected to the mass spectrometry after dilution to 1.0 μM. The results are shown in FIG. 2.

Figure 2:
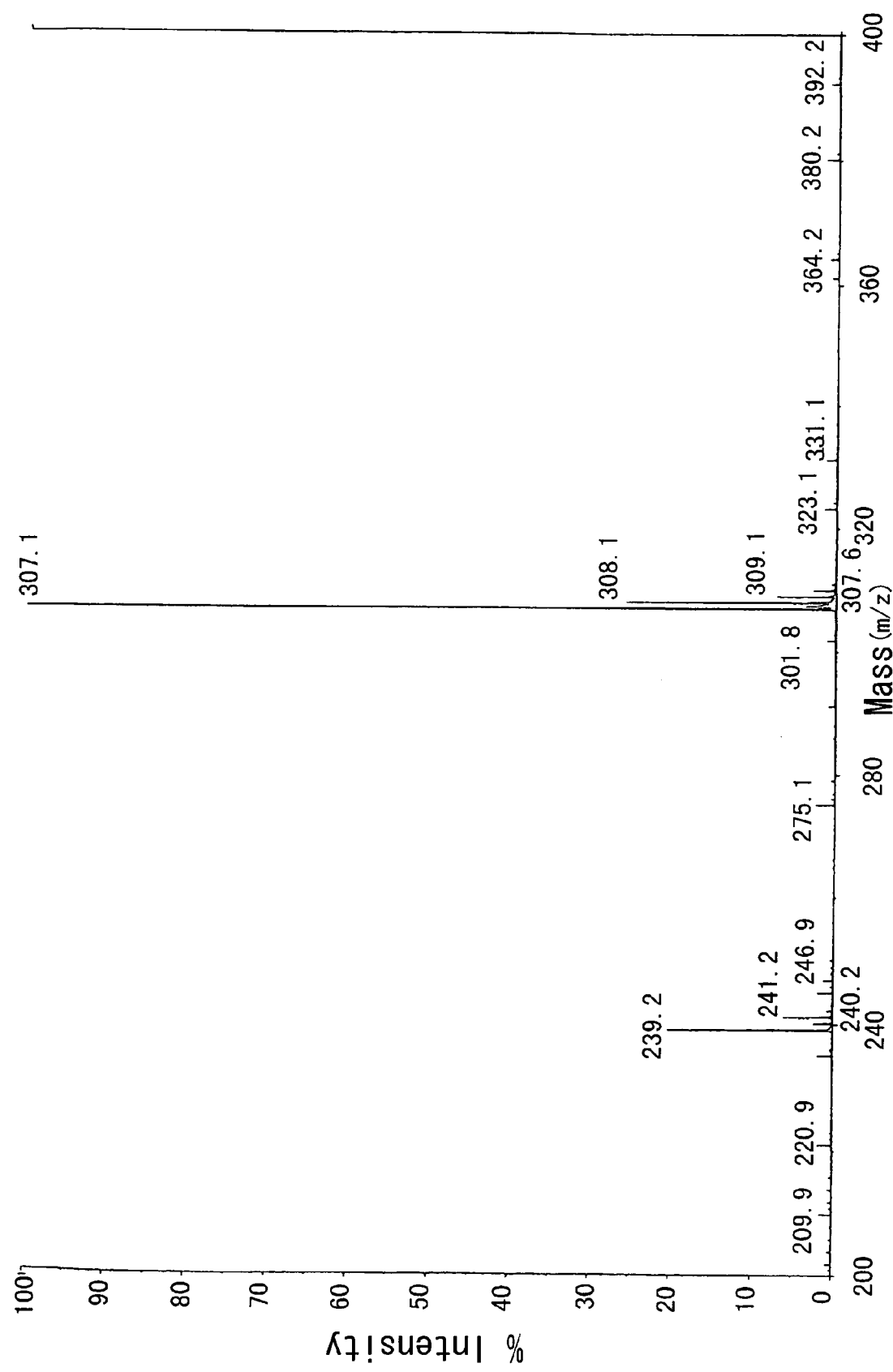
FIG. 2 shows the mass spectrum obtained in the electrospray ionization mass spectrometry carried out in Example 11 according to the present invention, wherein the probe alone was subjected to the electrospray ionization mass spectrometry.

As is apparent from FIGS. 1 and 2, the binding product between the sample compound and the probe exhibited a sharp peak at a position different from that obtained with the probe alone. By this, it was proved that electrospray ionization mass spectrometry may be carried out with high sensitivity and high accuracy by the method described above.

The invention claimed is:

1. A method for mass spectrometry, comprising binding a probe for mass spectrometry of liquid samples, which is represented by the Formula [I]:

$$R^2\text{-}A\text{-}R^1 \quad [\text{I}]$$

(wherein $R^1$ represents an ionic functional group which becomes an ion in a solvent, $R^2$ represents a structure which can bind to other substances, and A represents a spacer moiety)
and further wherein said A is represented by the following Formula [III]:

[III]

(wherein $R^6$ represents $C_1$-$C_{20}$ alkylene with the proviso that not less than one and not more than half of the —$CH_2$— units therein may be substituted by one or more groups selected from the group consisting of —O—, —CO— and —NH—, and that said alkylene may be substituted by one or more $C_1$-$C_{20}$ alkyl; and Ar represents an aromatic ring which may be substituted by 1 to 5 $C_1$-$C_{20}$ alkyl)
to a sample compound in a sample liquid; and subjecting the obtained bound product to mass spectrometry.

2. The method according to claim 1, wherein said $R^2$ is a functional group which can react with said substance so as to covalently bind to said substance.

3. The method according to claim 2, wherein said $R^1$ is an amine, carboxylic acid or a salt thereof, sulfonic acid or a salt thereof, or

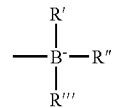

(wherein R', R" and R'" independently represent hydrogen, halogen or $C_1$-$C_{20}$ linear or branched alkyl).

4. The method according to claim 3, wherein said $R^1$ is an amine represented by Formula [II]:

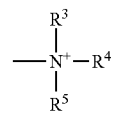

(wherein $R^3$, $R^4$ and $R^5$ independently represent hydrogen, halogen or $C_1$-$C_{20}$ linear or branched alkyl).

5. A method for mass spectrometry, comprising binding a probe for mass spectrometry of liquid samples, which is represented by the Formula [I]:

$$R^2\text{-}A\text{-}R^1 \quad [\text{I}]$$

(wherein $R^1$ represents an ionic functional group which becomes an ion in a solvent, $R^2$ represents a structure which can bind to other substance, and A represents a spacer moiety)
to a sample compound in a sample liquid; and subjecting the obtained bound product to mass spectrometry, wherein said $R^2$ is

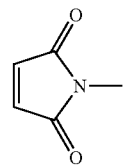

ClOC—, $CH_3CH(NH_2)$=CH—, —$CH_2ONH_2$—HCl, —$NHNH_2$,

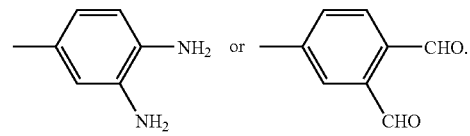

6. The method according to claims 2 or 5, wherein said A has a hydrophobic moiety and a hydrophilic moiety.

7. The method according to claim 5, wherein said A is represented by the following Formula [III]:

[III]

(wherein $R^6$ represents $C_1$-$C_{20}$ alkylene with the proviso that not less than one and not more than half of the —$CH_2$— units therein may be substituted by one or more groups selected from the group consisting of —O—, —CO— and —NH—, and that said alkylene may be substituted by one or more $C_1$-$C_{20}$ alkyl; and Ar represents an aromatic ring which may be substituted by 1 to 5 $C_1$-$C_{20}$ alkyl).

8. The method according to claim 4, wherein said A is represented by the following Formula [IV]:

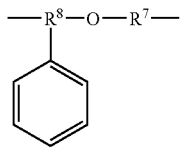

[IV]

(wherein $R^7$ may or may not exist, and when it exists, it represents $C_1$-$C_6$ alkylene; and $R^8$ represents $C_1$-$C_6$ alkylene in which an arbitrary hydrogen is substituted by the benzene ring shown in Formula [IV]), or represented by the following Formula [V]:

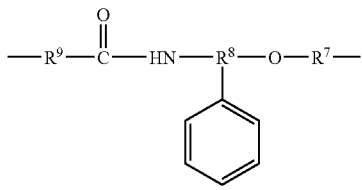

[V]

(wherein $R^7$ and $R^8$ represent the same meanings as in Formula [IV]; $R^9$ may or may not exist, and when it exists, it represents $C_1$-$C_6$ alkylene).

9. The method according to claims 2 or 5, which has a molecular weight of not more than 1000.

10. The method according to claims 2 or 5, which is for electrospray ionization mass spectrometry.

11. A method for mass spectrometry, comprising binding a probe for mass spectrometry of liquid samples, which is represented by the Formula [I]:

$R^2$-A-$R^1$  [I]

(wherein $R^1$ represents an ionic functional group which becomes an ion in a solvent, $R^2$ represents a structure which can bind to other substance, and A represents a spacer moiety)
to a sample compound in a sample liquid; and subjecting the obtained bound product to mass spectrometry, wherein said $R^2$ is represented by Formula [VI]:

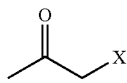

[VI]

(wherein X represents halogen), or

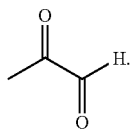

12. The method according to claim 2, wherein said $R^2$ has a group having optical activity.

13. The method according to claim 2, wherein said $R^2$ is represented by Formula [VIII]:

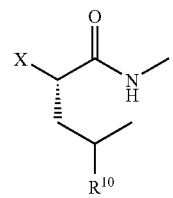

[VIII]

(wherein X represents halogen, and $R^{10}$ represents $C_1$-$C_5$ alkyl).

14. The method according to claim 1, wherein said $R^2$ has a structure which intercalates into double-stranded nucleic acids.

15. The method according to claim 14, wherein said $R^2$ is represented by Formula [IX]:

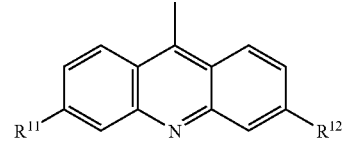

[IX]

(wherein $R^{11}$ and $R^{12}$ independently represent hydrogen, halogen, $C_1$-$C_5$ alkyl or $C_1$-$C_5$ N,N-dialkylamino).

16. The method according to claim 1, wherein said $R^2$ has a cyclic structure which can clathrate other substance.

17. The method according to claim 16, wherein said $R^2$ is represented by Formula [X]:

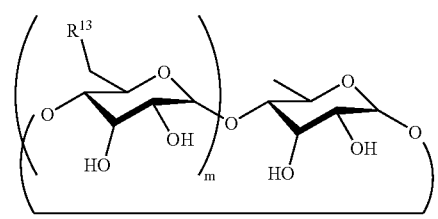

[X]

(wherein $R^{13}$ represents hydroxyl, carboxyl or $C_1$-$C_5$ alkyl; and m represents an integer of 5 to 9).

18. The method according to claim 16, wherein said $R^2$ is represented by Formula [XI]:

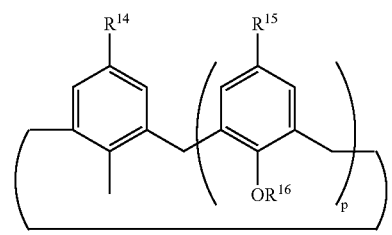

[XI]

(wherein $R^{14}$ and $R^{15}$ independently represent hydrogen, halogen or $C_1$-$C_5$ alkyl; $R^{16}$ represents $C_1$-$C_5$ alkyl or $C_1$-$C_5$ alkyl which has a carboxyl group, ester group or an amide group at its terminal; and p represents an integer of 3 to 7).

19. The method according to claim 11, wherein said $R^1$ is an carboxylic acid or a salt thereof, sulfonic acid or a salt thereof, or

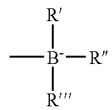

(wherein R', R" and R'" independently represent hydrogen, halogen or $C_1$-$C_{20}$ linear or branched alkyl).

20. The method according to claim 19, wherein said $R^1$ is a amine represented by Formula [II]:

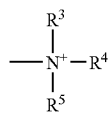

(wherein $R^3$, $R^4$ and $R^5$ independently represent hydrogen, halogen or $C_1$-$C_{20}$ linear or branched alkyl).

21. The method according to claim 11, wherein said A has a hydrophobic moiety and a hydrophilic moiety.

22. The method according to claim 4, wherein said A is represented by the following Formula [III]:

[III]

(wherein $R^6$ represents $C_1$-$C_{20}$ alkylene with the proviso that not less than one and not more than half of the —$CH_2$— units therein may be substituted by one or more groups selected from the group consisting of —O—, —CO— and —NH—, and that said alkylene may be substituted by one or more $C_1$-$C_{20}$ alkyl; and Ar represents an aromatic ring which may be substituted by 1 to 5 $C_1$-$C_{20}$ alkyl).

23. The method according to claim 4, wherein said A is represented by the following Formula [IV]:

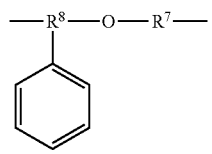

(wherein $R^7$ may or may not exist, and when it exists, it represents $C_1$-$C_6$ alkylene; and $R^8$ represents $C_1$-$C_6$ alkylene in which an arbitrary hydrogen is substituted by the benzene ring shown in Formula [IV]), or represented by the following Formula [V]:

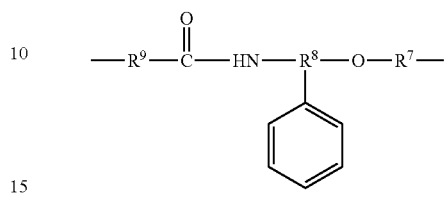

(wherein $R^7$ and $R^8$ represent the same meanings as in Formula [IV]; $R^9$ may or may not exist, and when it exists, it represents $C_1$-$C_6$ alkylene or phenylene).

24. The method according to any one of claims 1, 5 or 11, wherein said A represents —$R^6$— (wherein $R^6$ represents the same meanings as in Formula [III]) or —$R^6$—Ar—$R^{6'}$— wherein $R^6$ and Ar represent the same meanings as in Formula [III]; $R^{6'}$ may or may not exist, and when it exists, it represents the same meanings as said $R^6$ in Formula [III] (with the proviso that $R^6$ and $R^{6'}$ in said formula may be the same or different).

25. The method according to claim 24, wherein said A is represented by the following Formula [XII]:

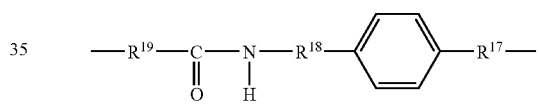

(wherein $R^{17}$ and $R^{18}$ independently represent $C_1$-$C_6$ alkylene; and $R^{19}$ may or may not exist, and when it exists, it represents $C_1$-$C_6$ alkylene);

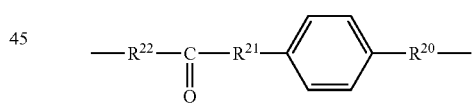

or represented by the following Formula [XIII]:

(wherein $R^{20}$ and $R^{21}$ independently represent $C_1$-$C_6$ alkylene; and $R^{22}$ may or may not exist, and when it exists, it represents $C_1$-$C_6$ alkylene).

26. The method according to claim 11, which has a molecular weight of not more than 1000.

27. The method according to claim 11, which is for electrospray ionization mass spectrometry.

\* \* \* \* \*